(12) United States Patent
Belko et al.

(10) Patent No.: US 8,557,876 B2
(45) Date of Patent: Oct. 15, 2013

(54) PYRIMIDINE DERIVATIVES AND THEIR USE IN PERFUME COMPOSITIONS

(75) Inventors: Robert P. Belko, Monroe, NJ (US); Paul D. Jones, Aberdeen, NJ (US); Anthony T. Levorse, Jr., Westfield, NJ (US); Michael G. Monteleone, Hazlet, NJ (US); Anubhav P. S. Narula, Hazlet, NJ (US); Franc T. Schiet, Naarden (NL)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 13/540,894

(22) Filed: Jul. 3, 2012

(65) Prior Publication Data

US 2012/0277325 A1 Nov. 1, 2012

Related U.S. Application Data

(63) Continuation-in-part of application No. 13/430,908, filed on Mar. 27, 2012, which is a continuation-in-part of application No. 13/027,314, filed on Feb. 15, 2011.

(51) Int. Cl.
*C07D 239/74* (2006.01)

(52) U.S. Cl.
USPC ........... 514/788; 544/249; 544/242; 544/344; 510/103; 512/10; 424/76.2

(58) Field of Classification Search
None
See application file for complete search history.

*Primary Examiner* — Andrew D Kosar
*Assistant Examiner* — John S Kenyon
(74) *Attorney, Agent, or Firm* — Elizabeth M. Quirk; XuFan Tseng; Joseph F. Leightner

(57) ABSTRACT

The present invention relates to novel pyrimidine derivatives and their use in perfume compositions. The novel pyrimidine derivatives of the present invention are represented by the following formula:

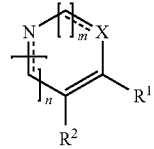

Formula I wherein m and n are integers that when m is 0, n is 1; when m is 1, n is 0 or 1; or when m is 2, n is 0;
wherein $(CH)_m$ and $(CH)_n$ are each independently optionally substituted with a substituent selected from the group consisting of methyl and ethyl;
wherein X is selected from the group consisting of N, O, and S; and
wherein $R^1$ and $R^2$ each independently represent H or a hydrocarbon group, or $R^1$ and $R^2$ together represent a fused ring or a ring system,
with the proviso that when $R^1$ is H, $R^2$ is not H.

11 Claims, No Drawings

PYRIMIDINE DERIVATIVES AND THEIR USE IN PERFUME COMPOSITIONS

STATUS OF RELATED APPLICATIONS

This application is a continuation-in-part of U.S. Ser. No. 13/430,908, filed Mar. 27, 2012, now pending, which is a continuation-in-part of U.S. Ser. No. 13/027,314, filed Feb. 15, 2011, now pending, the contents hereby incorporated by reference as if set forth in its entirety.

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how differences in the chemical structure of the molecule can result in significant differences in the odor, notes and characteristics of a molecule. These variations and the ongoing need to discover and use the new chemicals in the development of new fragrances allow the perfumers to apply the new compounds in creating new fragrances.

SUMMARY OF THE INVENTION

The present invention provides novel compounds and their unexpected advantageous use in enhancing, improving or modifying the fragrance of perfumes, colognes, toilet water, fabric care products, personal products and the like.

More specifically, the present invention relates to novel pyrimidine derivatives represented by Formula I set forth below:

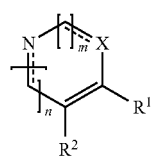

Formula I wherein m and n are integers that when m is 0, n is 1; when m is 1, n is 0 or 1; or when m is 2, n is 0;

wherein $(CH)_m$ and $(CH)_n$ are each independently optionally substituted with a substituent selected from the group consisting of methyl and ethyl;

wherein X is selected from the group consisting of N, O, and S; and wherein $R^1$ and $R^2$ each independently represent H or a hydrocarbon group, or $R^1$ and $R^2$ together represent a fused ring or a ring system, with the proviso that when $R^1$ is H, $R^2$ is not H.

Another embodiment of the present invention relates to a subgenus of pyrimidine derivatives represented by Formula II set forth below:

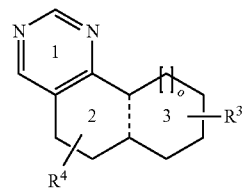

Formula II wherein a pyrimidine ring 1 is attached to a proximal ring 2, and wherein the proximal ring 2 is attached to a distal ring 3;

wherein o is an integer of 0 or 1;

wherein $R^3$ represents a substituent in any position of the distal ring 3 and is selected from the group consisting of H, methyl, and ethyl;

wherein $R^4$ represents a substituent in any position of the proximal ring 2 and is H or methyl; and wherein the broken line represents a single or double bond, with the proviso that when $R^3$ is H, $R^4$ is not H.

Another embodiment of the present invention relates to a subgenus of pyrimidine derivatives represented by Formula III set forth below:

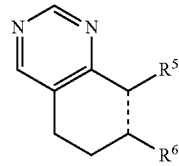

Formula III wherein $R^5$ and $R^6$ each independently represent H or a $C_1$-$C_6$ straight or branched, saturated or unsaturated hydrocarbon group; and wherein the broken line represents a single or double bond, with the proviso that $R^5$ and $R^6$ together contain 3-10 carbon atoms.

Another embodiment of the present invention relates to a subgenus of pyrimidine derivatives represented by Formula IV set forth below:

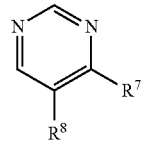

Formula IV wherein $R^7$ and $R^8$ each independently represent H or a $C_1$-$C_8$ straight or branched, saturated or unsaturated hydrocarbon group, with the proviso that $R^7$ and $R^8$ together contain 4-8 carbon atoms.

Another embodiment of the present invention relates to a subgenus of pyrimidine derivatives represented by Formula V set forth below:

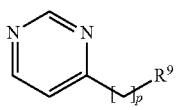

Formula V wherein p is an integer selected from the group consisting of 0, 1, and 2; and wherein $R^9$ represents a 5 to 6 membered saturated or unsaturated hydrocarbon ring substituted with a substituent selected from the group consisting of methyl and ethyl.

Another embodiment of the present invention relates to a subgenus of pyrimidine derivatives represented by Formula VI set forth below:

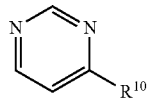

Formula VI wherein $R^{10}$ represents

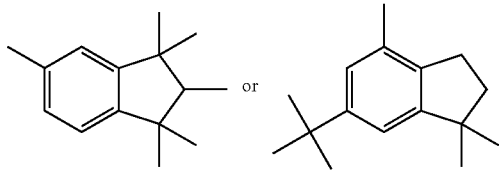

Another embodiment of the present invention relates to a subgenus of pyrimidine derivatives represented by Formula VII set forth below:

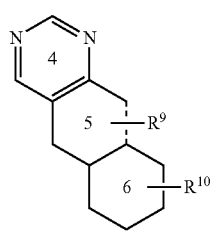

Formula VII wherein a pyrimidine ring 4 is attached to a proximal ring 5, and wherein the proximal ring 5 is attached to a distal ring 6;

wherein $R^9$ represents a substituent in any position of the proximal ring 5 and is selected from the group consisting of H, methyl, and ethyl;

wherein $R^{10}$ represents a substituent in any position of the distal ring 6 and is selected from the group consisting of H, methyl, and ethyl; and wherein the broken line represents a single or double bond, with the proviso that $R^9$ and $R^{10}$ together contain at least two carbon atoms.

Another embodiment of the present invention relates to a subgenus of pyrimidine derivatives represented by Formula VIII set forth below:

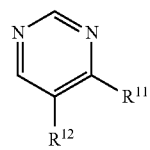

Formula VIII wherein $R^{11}$ and $R^{12}$ taken together represent

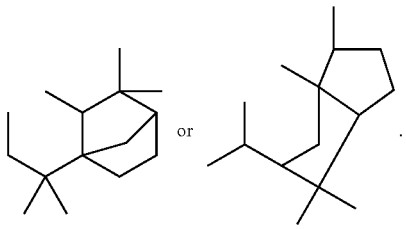

Another embodiment of the present invention relates to a subgenus of pyrimidine derivatives represented by Formula IX set forth below:

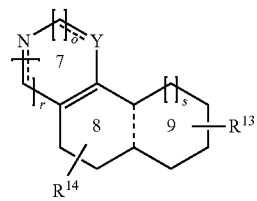

Formula IX wherein a ring 7 is attached to a proximal ring 8, and wherein the proximal ring 8 is attached to a distal ring 9;

wherein q and r are each independently integers of 0 or 1 that when q is 0, r is 1; or when q is 1, r is 0 or 1;

wherein s represents an integer of 0 or 1;

wherein Y represents O or S;

wherein $R^{13}$ represents a substituent in any position of the distal ring 9 and is selected from the group consisting of H, methyl, and ethyl;

wherein $R^{14}$ represents a substituent in any position of the proximal ring 8 and is H or methyl; and wherein the broken line represents a single or double bond, with the proviso that when $R^{13}$ is H, $R^{14}$ is not H.

Another embodiment of the present invention relates to a subgenus of pyrimidine derivatives represented by Formula X set forth below:

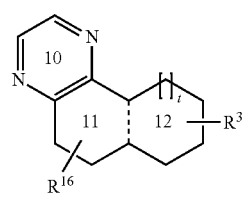

Formula X wherein a pyrazine ring 10 is attached to a proximal ring 11, and wherein the proximal ring 11 is attached to a distal ring 12;

wherein t represents an integer of 0 or 1;

wherein $R^{15}$ represents a substituent in any position of the distal ring 12 and is selected from the group consisting of H, methyl, and ethyl;

wherein $R^{16}$ represents a substituent in any position of the proximal ring 11 and is H or methyl; and wherein the broken line represents a single or double bond, with the proviso that when $R^{15}$ is H, $R^{16}$ is not H.

Another embodiment of the present invention relates to a fragrance composition comprising the novel compounds provided above.

Another embodiment of the present invention relates to a fragrance product comprising the compounds provided above.

Another embodiment of the present invention relates to a method of improving, enhancing or modifying a fragrance formulation through the addition of an olfactory acceptable amount of the novel compounds provided above.

These and other embodiments of the present invention will be apparent by reading the following specification.

DETAILED DESCRIPTION OF THE INVENTION

The novel pyrimidine derivatives represented by Formula I of the present invention are illustrated, for example, by following examples.

1,1,2,3,3-Pentamethyl-2,3,4,5-tetrahydro-1H-7,9-diaza-cyclopenta[a]naphthalene:

Structure 1

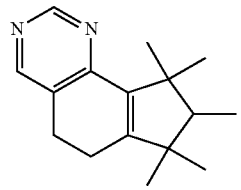

1,1,2,3,3-Pentamethyl-2,3,3a,4,5,9b-hexahydro-1H-7,9-diaza-cyclopenta[a]naphthalene:

Structure 2

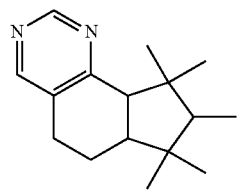

1,1,3,3-Tetramethyl-2,3,4,5-tetrahydro-1H-7,9-diaza-cyclopenta[a]naphthalene:

Structure 3

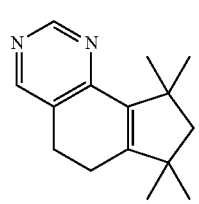

1,1,3,3-Tetramethyl-2,3,3a,4,5,9b-hexahydro-1H-7,9-diaza-cyclopenta[a]naphthalene:

Structure 4

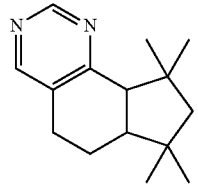

1,1,2,3,3,5-Hexamethyl-2,3,4,5-tetrahydro-1H-7,9-diaza-cyclopenta[a]naphthalene:

Structure 5

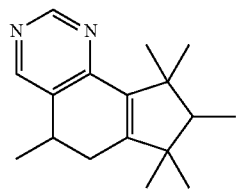

1,1,2,3,3,5-Hexamethyl-2,3,3a,4,5,9b-hexahydro-1H-7,9-diaza-cyclopenta[a]naphthalene:

Structure 6

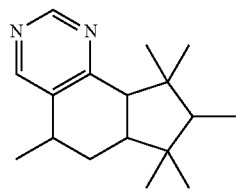

7,7,10,10-Tetramethyl-5,6,7,8,9,10-hexahydro-benzo[h]quinazoline:

Structure 7

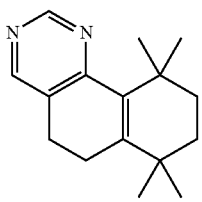

7,7,10,10-Tetramethyl-5,6,6a,7,8,9,10,10a-octahydro-benzo[h]quinazoline:

Structure 8

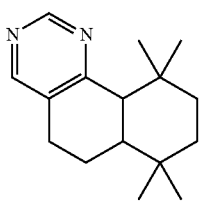

5,7,7,8,10,10-Hexamethyl-5,6,7,8,9,10-hexahydro-benzo[h]quinazoline:

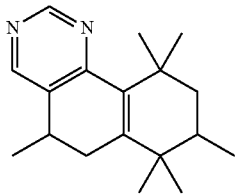

Structure 9

5,7,7,8,10,10-Hexamethyl-5,6,6a,7,8,9,10,10a-octahydro-benzo[h]quinazoline:

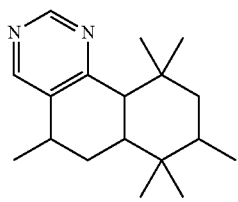

Structure 10

7,7,10a-Trimethyl-5,6,6a,7,8,9,10,10a-octahydro-benzo[h]quinazoline:

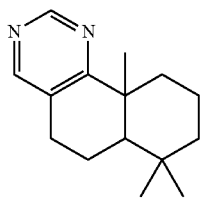

Structure 11

8-Isopropyl-5,6,7,8-tetrahydro-quinazoline:

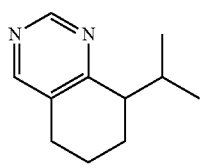

Structure 12

8-tert-Butyl-5,6,7,8-tetrahydro-quinazoline:

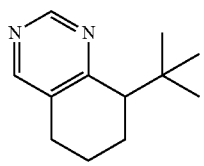

Structure 13

5-(1,5-Dimethyl-hex-4-enyl)-pyrimidine:

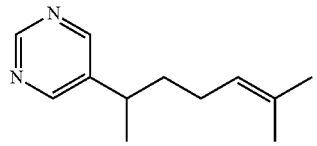

Structure 14

4-tert-Butyl-pyrimidine:

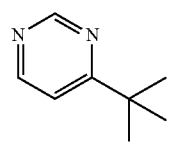

Structure 15

4-(2,2-Dimethyl-propyl)-pyrimidine:

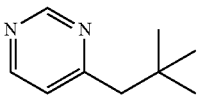

Structure 16

4,5-Diisopropyl-pyrimidine:

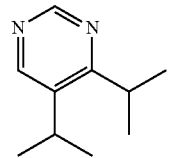

Structure 17

4,5-Di-tert-butyl-pyrimidine:

Structure 18

5-tert-Butyl-4-(2,2-dimethyl-propyl)-pyrimidine:

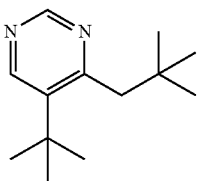

Structure 19

4-(2,6,6-Trimethyl-cyclohex-3-enyl)-pyrimidine

Structure 20

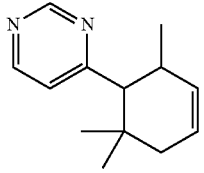

4-(3,3-Dimethyl-cyclohexyl)-pyrimidine:

Structure 21

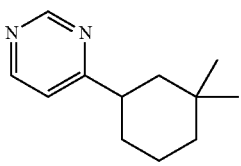

4-[2-(2,6,6-Trimethyl-cyclohex-1-enyl)-ethyl]-pyrimidine:

Structure 22

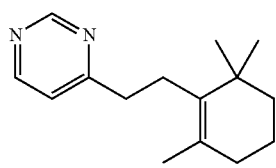

4-[2-(2,5,6,6-Tetramethyl-cyclohex-1-enyl)-ethyl]-pyrimidine:

Structure 23

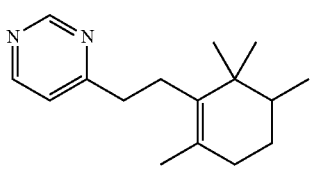

4-(1,1,2,3,3-Pentamethyl-indan-5-yl)-pyrimidine:

Structure 24

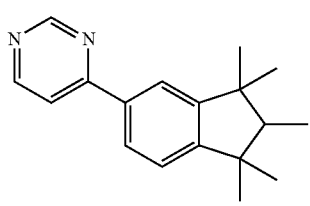

4-(6-tert-Butyl-1,1-dimethyl-indan-4-yl)-pyrimidine:

Structure 25

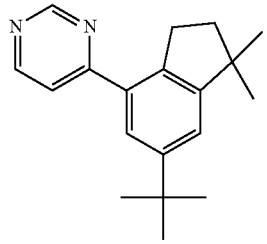

6,6,9a-Trimethyl-5,5a,6,7,8,9,9a,10-octahydro-benzo[g]quinazoline:

Structure 26

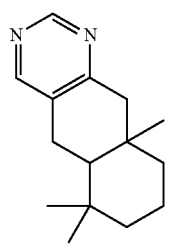

5a,10-Dimethyl-5,5a,6,7,8,9-hexahydro-benzo[g]quinazoline:

Structure 27

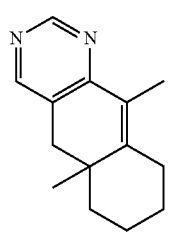

5a,10-Dimethyl-5,5a,6,7,8,9,9a,10-octahydro-benzo[g]quinazoline:

Structure 28

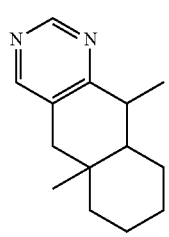

6,6,10,10-Tetramethyl-5,7,8,9,10,10a-hexahydro-6H-6a,9-methanobenzo[H]quinazoline:

Structure 29

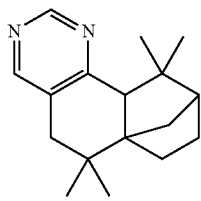

5,7,7,10-Tetramethyl-6,7,7a,8,9,10-hexahydro-5H-6,10a-methanoazuleno[5,4-d]pyrimidine:

Structure 30

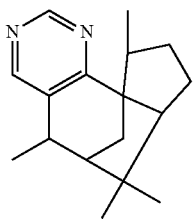

5,6,7,8-Tetrahydro-6,6,7,8,8-pentamethyl-4H-indeno[5,4-D]isoxazole:

Structure 31

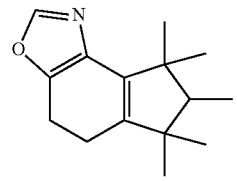

5,5a,6,7,8,8a-hexahydro-6,6,7,8,8-pentamethyl-4H-indeno[5,4-D]isoxazole:

Structure 32

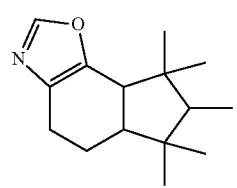

6,6,7,8,8-Pentamethyl-5,6,7,8-tetrahydro-4H-1-oxa-3-aza-as-indacene:

Structure 33

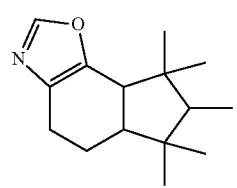

6,6,7,8,8-Pentamethyl-5,6,7,8-tetrahydro-4H-indeno[4,5-d]oxazole:

Structure 34

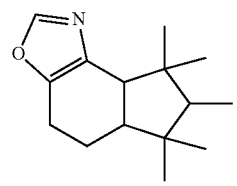

6,6,7,8,8-Pentamethyl-5,5a,6,7,8,8a-hexahydro-4H-1-oxa-3-aza-as-indace:

Structure 35

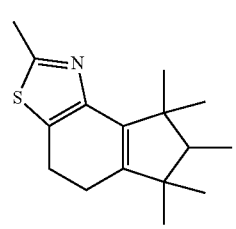

6,6,7,8,8-Pentamethyl-5,5a,6,7,8,8a-hexahydro-4H-indeno[4,5-d]oxazole:

Structure 36

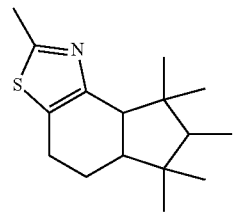

2,6,6,7,8,8-Hexamethyl-5,6,7,8-tetrahydro-4H-3-thia-1-aza-as-indacene:

Structure 37

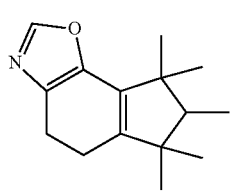

2,6,6,7,8,8-Hexamethyl-5,5a,6,7,8,8a-hexahydro-4H-3-thia-1-aza-as-indacene:

Structure 38

7,7,8,9,9-Pentamethyl-5,7,8,9-tetrahydro-6H-cyclopenta[f]quinoxaline:

Structure 39

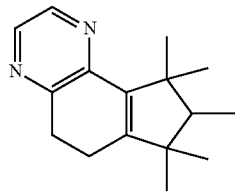

7,7,8,9,9-Pentamethyl-5,6a,7,8,9,9a-hexahydro-6H-cyclopenta[f]quinoxaline:

Structure 40

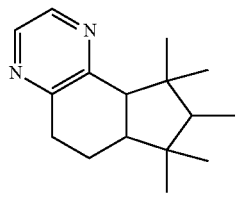

Those with skill in the art will recognize that the compounds of the present invention contain chiral centers, thereby providing a number of isomers of the claimed compounds. For example, the compounds of Structure 1 and Structure 2 described in the above contain chiral centers indicated with asterisks (*) in the following:

Structure 1

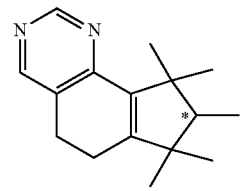

Structure 2

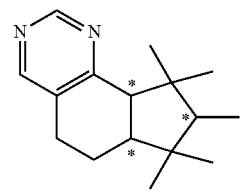

Thus, the isomeric forms of Structure 1 and Structure 2 may be further represented, respectively, by the following structures:

Structure 1a

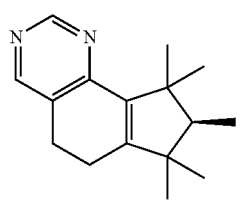

Structure 1b

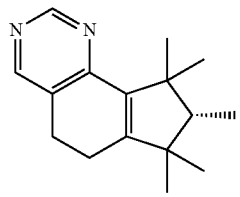

Structure 2a

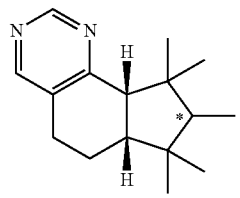

Structure 2b

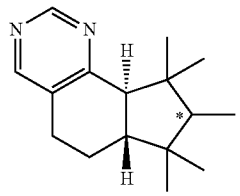

Structure 1a represents 2S-1,1,2,3,3-pentamethyl-2,3,4,5-tetrahydro-1H-7,9-diaza-cyclopenta[a]naphthalene;

Structure 1b represents 2R-1,1,2,3,3-pentamethyl-2,3,4,5-tetrahydro-1H-7,9-diaza-cyclopenta[a]naphthalene;

Structure 2a represents diastereomeric mixture cis-1,1,2,3,3-pentamethyl-2,3,3a,4,5,9b-hexahydro-1H-7,9-diaza-cyclopenta[a]naphthalene; and Structure 2b represents diastereomeric mixture trans-1,1,2,3,3-pentamethyl-2,3,3a,4,5,9b-hexahydro-1H-7,9-diaza-cyclopenta[a]naphthalene.

It is intended herein that the compounds described herein include isomeric mixtures of such compounds, as well as those isomers that may be separated using techniques known to those having skill in the art. Suitable techniques include chromatography such as high performance liquid chromatography, referred to as HPLC, and particularly silica gel chromatography and gas chromatography trapping known as GC trapping. Yet, commercial products are mostly offered as isomeric mixtures.

The preparation of the compounds of the present invention is detailed in the Examples. Materials were purchased from Aldrich Chemical Company unless noted otherwise.

The use of the compounds of the present invention is widely applicable in current perfumery products, including the preparation of perfumes and colognes, the perfuming of personal care products such as soaps, shower gels, and hair care products, fabric care products, air fresheners, and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art. Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

The compounds of the present invention can be used in combination with a complementary fragrance compound. The term "complementary fragrance compound" as used herein is defined as a fragrance compound selected from the group consisting of 2[(4-methylphenyl)methylene]-heptanal (Acalea), iso-amyl oxyacetic acid allylester (Allyl Amyl Glycolate), (3,3-dimethylcyclohexyl)ethyl ethyl propane-1,3-dioate (Applelide), (E/Z)-1-ethoxy-1-decene (Arctical), 2-ethyl-4-(2,2,3-trimethyl-3-cyclo-penten-1-yl)-2-buten-1-ol (Bacdanol), 2-methyl-3-[(1,7,7-trimethylbicyclo[2.2.1]hept-2-yl)oxy]exo-1-propanol (Bornafix), 1,2,3,5,6,7-hexahydro-1,1,2,3,3-pentamethyl-4H-inden-4-one (Cashmeran), trimethylcyclopentenylmethyloxabicyclooctane (Cassiffix), 1,1-dimethoxy-3,7-dimethyl-2,6-octadiene (Citral DMA), 3,7-dimethyl-6-octen-1-ol (Citronellol), 3A,4,5,6,7,7A-hexahydro-4,7-methano-1H-inden-5/6-yl acetate (Cyclacet), 3A,4,5,6,7,7A-hexahydro-4,7-methano-1H-inden-5/6-yl propinoate (Cyclaprop), 3A,4,5,6,7,7A-hexahydro-4,7-methano-1G-inden-5/6-yl butyrate (Cyclobutanate), 1-(2,6,6-trimethyl-3-cyclohexen-1-yl)-2-buten-1-one (Delta Damascone), 3-(4-ethylphenyl)-2,2-dimethyl propanenitrile (Fleuranil), 3-(O/P-ethylphenyl) 2,2-dimethyl propionaldehyde (Floralozone), tetrahydro-4-methyl-2-(2-methylpropyl)-2H-pyran-4-ol (Floriffol), 1,3,4,6,7,8-hexahydro-4,6,6,7,8,8-hexamethylcyclopenta-gamma-2-benzopyran (Galaxolide), 1-(5,5-dimethyl-1-cyclohexen-1-yl)pent-4-en-1-one (Galbascone), E/Z-3,7-dimethyl-2,6-octadien-1-yl acetate (Geranyl Acetate), α-methyl-1,3-benzodioxole-5-propanal (Helional), 1-(2,6,6-trimethyl-2-cyclohexen-1-yl)-1,6-heptadien-3-one (Hexylon), (Z)-3-hexenyl-2-hydroxybenzoate (Hexenyl Salicylate, CIS-3), 4-(2,6,6-trimethyl-2-cyclohexen-1-yl)-3-buten-2-one (Ionone α), 1-(1,2,3,4,5,6,7,8-octahydro-2,3,8,8-tetramethyl-2-naphthalenyl)-ethan-1-one (Iso E Super), methyl 3-oxo-2-pentylcyclopentaneacetate (Kharismal), 2,2,4-trimethyl-4-phenyl-butanenitrile (Khusinil), 3,4,5,6,6-pentamethylhept-3-en-2-one (Koavone), 3/4-(4-hydroxy-4-methylpentyl)cyclohexene-1-carboxaldehyde (Lyral), 3-methyl-4-(2,6,6-trimethyl-2-cyclohexen-1-yl)-3-buten-2-one (Methyl Ionone γ), 1-(2,6,6-trimethyl-2-cyclohexen-1-yl)pent-1-en-3-one (Methyl Ionone α Extra, Methyl Ionone N), 3-methyl-4-phenylbutan-2-ol (Muguesia), cyclopentadec-4-en-1-one (Musk Z4), 3,3,4,5,5-pentamethyl-11,13-dioxatricyclo[7.4.0.0<2,6>]tridec-2(6)-ene (Nebulone), 3,7-dimethyl-2,6-octadien-1-yl acetate (Neryl Acetate), 3,7-dimethyl-1,3,6-octatriene (Ocimene), ortho-tolylethanol (Peomosa), 3-methyl-5-phenylpentanol (Phenoxanol), 1-methyl-4-(4-methyl-3-pentenyl)cyclohex-3-ene-1-carboxaldehyde (Precyclemone B), 4-methyl-8-methylene-2-adamantanol (Prismantol), 2-ethyl-4-(2,2,3-trimethyl-3-cyclopenten-1-yl)-2-buten-1-ol (Sanjinol), 2-methyl-4-(2,2,3-trimethyl-3-cyclopenten-1-yl)-2-buten-1-ol (Santaliff), Terpineol, 2,4-dimethyl-3-cyclohexene-1-carboxaldehyde (Triplal), decahydro-2,6,6,7,8,8-hexamethyl-2H-indeno[4,5-B]furan (Trisamber), 2-tert-butylcyclohexyl acetate (Verdox), 4-tert-butylcyclohexyL acetate (Vertenex), acetyl cedrene (Vertofix), 3,6/4,6-dimethylcyclohex-3-ene-1-carboxaldehyde (Vertoliff), and (3Z)-1-[(2-methyl-2-propenyl)oxy]-3-hexene (Vivaldie).

The term "hydrocarbon group" means a chemical group that contains only hydrogen and carbon atoms. The hydrocarbon group of the present invention can be a straight, branched and/or cyclic, saturated or unsaturated group.

The terms "fragrance formulation", "fragrance composition", and "perfume composition" mean the same and refer to a consumer composition that is a mixture of compounds including, for example, alcohols, aldehydes, ketones, esters, ethers, lactones, nitriles, natural oils, synthetic oils, and mercaptans, which are admixed so that the combined odors of the individual components produce a pleasant or desired fragrance. The fragrance formulation of the present invention is a consumer composition comprising a compound of the present invention. The fragrance formulation of the present invention comprises a compound of the present invention and further a complementary fragrance compound as defined above.

The term "fragrance product" means a consumer product that adds a fragrance or masks a malodor. Fragrance products may include, for example, perfumes, colognes, personal care products such as soaps, shower gels, and hair care products, fabric products, air fresheners, cosmetic preparations, and perfume cleaning agents such as detergents, dishwashing materials, scrubbing compositions, and window cleaners. The fragrance product of the present invention is a consumer product that contains a compound of the present invention. The fragrance product of the present invention contains a compound of the present invention and further a complementary fragrance compound as defined above.

The term "improving" in the phrase "improving, enhancing or modifying a fragrance formulation" is understood to mean raising the fragrance formulation to a more desirable character. The term "enhancing" is understood to mean making the fragrance formulation greater in effectiveness or providing the fragrance formulation with an improved character. The term "modifying" is understood to mean providing the fragrance formulation with a change in character.

The term "olfactory acceptable amount" is understood to mean the amount of a compound in a fragrance formulation, wherein the compound will contribute its individual olfactory characteristics. However, the olfactory effect of the fragrance formulation will be the sum of effect of each of the fragrance ingredients. Thus, the compound of the present invention can be used to improve or enhance the aroma characteristics of the fragrance formulation, or by modifying the olfactory reaction contributed by other ingredients in the formulation. The olfactory acceptable amount may vary depending on many factors including other ingredients, their relative amounts and the olfactory effect that is desired.

The amount of the compounds of the present invention employed in a fragrance formulation varies from about 0.005 to about 70 weight percent, preferably from 0.005 to about 50 weight percent, more preferably from about 0.5 to about 25 weight percent, and even more preferably from about 1 to about 10 weight percent. Those with skill in the art will be able to employ the desired amount to provide desired fragrance effect and intensity. In addition to the compounds of the present invention, other materials can also be used in conjunction with the fragrance formulation. Well known materials such as surfactants, emulsifiers, polymers to encapsulate the fragrance can also be employed without departing from the scope of the present invention.

When used in a fragrance formulation these ingredients provide additional notes to make a fragrance formulation more desirable and noticeable, and add the perception of value. The odor qualities found in these materials assist in beautifying and enhancing the finished accord as well as improving the performance of the other materials in the fragrance.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million, L is understood to be liter, mL is understood to be milliliter, Kg is understood to be kilogram, g is understood to be gram, mol is understood to be mole, psi is understood to be pound-force per square inch, and mmHg be millimeters (mm) of mercury (Hg). IFF as used in the examples is understood to mean International Flavors & Fragrances Inc., New York, N.Y., USA.

EXAMPLE I

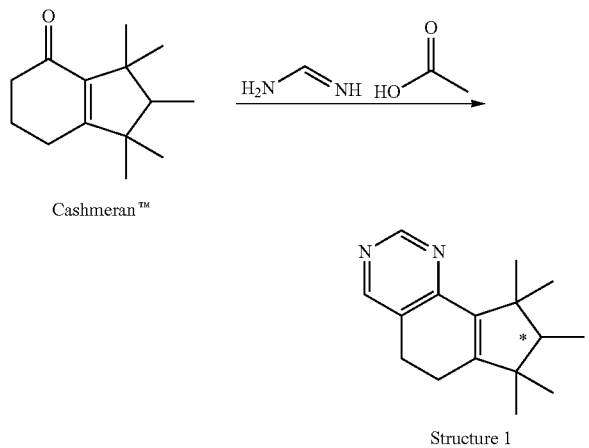

Structure 1

Preparation of 1,1,3,3-Pentamethyl-2,3,4,5-tetrahydro-1H-7,9-diaza-cyclopenta[a]naphthalene (Structure 1): A 5 L reaction vessel was charged with Cashmeran™ (412 g, 2.0 mol, commercially available at IFF), formamidine acetate ($HN_2CH=NH/HOOCCH_3$) (1.03 Kg, 10.0 mol), and butanol (1.2 L). The reaction mixture was heated to 118° C. for 4 hours and then cooled to 25° C. The reaction mixture was washed twice with brine (1 L) and purified by vacuum distillation to afford 1,1,2,3,3-pentamethyl-2,3,4,5-tetrahydro-1H-7,9-diaza-cyclopenta[a]naphthalene (260 g) having a boiling point of 140° C. at a pressure of 1.6 mmHg. Further recrystallization from ethanol afforded a solid with a melting point of 80.0° C.

$^1$H NMR ($CDCl_3$, 500 MHz): 8.90 ppm (s, 1H), 8.31 ppm (s, 1H), 2.77-2.82 ppm (m, 2H), 2.35-2.41 ppm (m, 1H), 2.25-2.32 ppm (m, 1H), 1.74 ppm (q, 1H, J=7.37 Hz), 1.38 ppm (s, 3H), 1.23 ppm (s, 3H), 1.11 ppm (s, 3H), 0.95 ppm (d, 3H, J=7.40 Hz), 0.93 ppm (s, 3H).

Structure 1 was described as having musky, ambery, and powdery notes.

EXAMPLE II

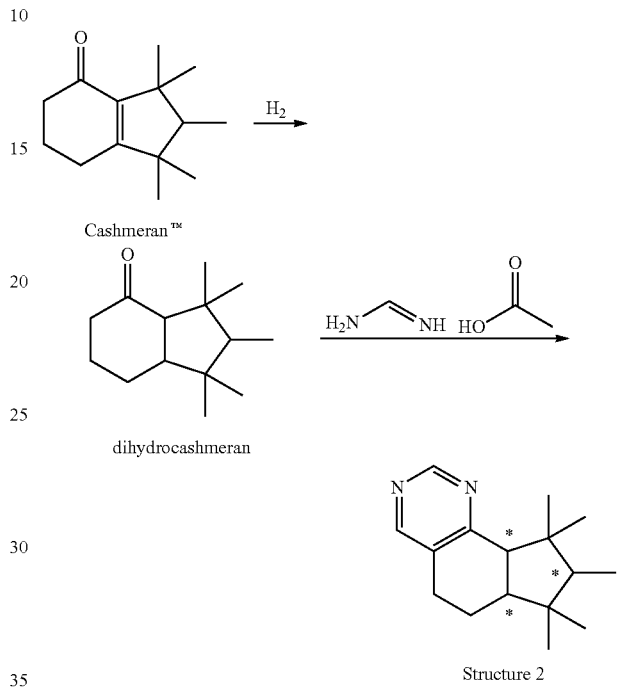

Structure 2

Preparation of 1,1,2,3,3-Pentamethyl-2,3,3a,4,5,9b-hexahydro-1H-7,9-diaza-cyclopenta[a]naphthalene (Structure 2): Dihydrocashmeran was obtained via the hydrogenation of Cashmeran™. A 3 L reaction vessel was charged with dihydrocashmeran (255 g, 1.2 mol), formamidine acetate (642 g, 6.2 mol), and butanol (1.2 L). The reaction mixture was heated to 118° C. for 4 hours and then cooled to 25° C. The reaction mixture was washed twice with brine (1 L) and purified by vacuum distillation to afford a 40:60 cis/trans mixture of 1,1,2,3,3-pentamethyl-2,3,3a,4,5,9b-hexahydro-1H-7,9-diaza-cyclopenta[a]naphthalene (200 g) having a boiling point of 153° C. at a pressure of 2.0 mmHg. The cis/trans structures were confirmed by NMR analysis by GC trapping.

Cis-1,1,2,3,3-pentamethyl-2,3,3a,4,5,9b-hexahydro-1H-7,9-diaza-cyclopenta[a]naphthalene:

$^1$H NMR ($CDCl_3$, 500 MHz): 8.96 ppm (s, 1H), 8.39 ppm (s, 1H), 3.00 ppm (d, J=9.7 Hz, 1H), 2.52-2.79 ppm (m, 2H), 1.25-2.15 ppm (m, 4H), 1.42 ppm (s, 3H), 1.10 ppm (s, 3H), 0.92 ppm (s, 3H), 0.84 ppm (d, J=7.3 Hz, 3H), 0.54 ppm (s, 3H).

Trans-1,1,2,3,3-pentamethyl-2,3,3a,4,5,9b-hexahydro-1H-7,9-diaza-cyclopenta[a]naphthalene:

$^1$H NMR ($CDCl_3$, 500 MHz): 8.92 ppm (s, 1H), 8.37 ppm (s, 1H), 2.75-2.93 ppm (m, 2H), 2.65 ppm (d, J=12.6 Hz, 1H), 1.20-2.10 ppm (m, 4H), 1.32 ppm (s, 3H), 0.99 ppm (s, 3H), 0.95 ppm (s, 3H), 0.84 ppm (d, J=7.5 Hz, 3H), 0.71 ppm (s, 3H).

Structure 2 was described as having ambery, musky, and woody notes.

EXAMPLE III

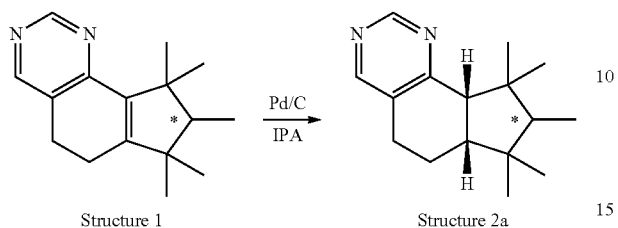

Structure 1       Structure 2a

Preparation of Cis-1,1,3,3-pentamethyl-2,3,3a,4,5,9b-hexahydro-1H-7,9-diaza-cyclopenta[a]naphthalene (Structure 2a): A 500 mL zipper autoclave was charged with 1,1,2,3,3-pentamethyl-2,3,4,5-tetrahydro-1H-7,9-diaza-cyclopenta[a]naphthalene (100 g, prepared as above in EXAMPLE I), IPA (100 mL), and palladium on carbon (Pd/C) (1 g). The autoclave was sealed, purged with nitrogen, and then pressurized with hydrogen. The reaction mixture was heated to 180° C. for 4 hours and subsequently cooled to 25° C. The autoclave was vented and purged with nitrogen. The catalyst was removed by filtration through celite. A crude mass containing the major product cis-1,1,2,3,3-pentamethyl-2,3,3a,4,5,9b-hexahydro-1H-7,9-diaza-cyclopenta[a]naphthalene (90%) was obtained. The crude mass was evaluated by gas chromatography olfactometry. Cis-1,1,2,3,3-pentamethyl-2,3,3a,4,5,9b-hexahydro-1H-7,9-diaza-cyclopenta[a]naphthalene was described as having a musky character. In addition, the minor product in the crude mass, trans-1,1,2,3,3-pentamethyl-2,3,3a,4,5,9b-hexahydro-1H-7,9-diaza-cyclopenta[a]naphthalene (Structure 2b) (10%), was also evaluated and described as having an ambery character.

EXAMPLE IV

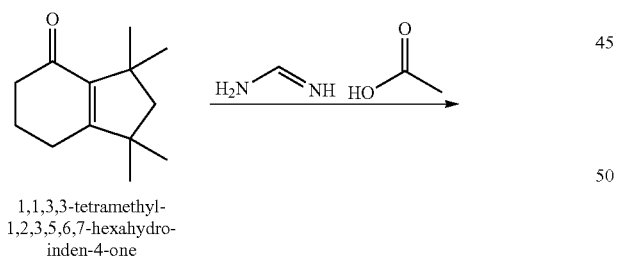

1,1,3,3-tetramethyl-1,2,3,5,6,7-hexahydro-inden-4-one

Structure 3

Preparation of 1,1,3,3-Tetramethyl-2,3,4,5-tetrahydro-1H-7,9-diaza-cyclopenta[a]naphthalene (Structure 3): A 100 mL reaction flask is charged with 1,1,3,3-tetramethyl-1,2,3,5,6,7-hexahydro-inden-4-one (prepared as described in U.S. Pat. No. 3,927,083) (10 g, 0.05 mol), formamidine acetate (27 g, 0.26 mol), and butanol ($C_4H_9OH$) (50 mL). The reaction mixture is heated to 130° C. and stirred for 24 hours. The crude mass is washed once with aqueous sulfuric acid ($H_2SO_4$) (10%, 100 mL) followed by twice with brine (30 mL). Butanol is recovered by roto-evaporation. The crude product is further purified with liquid chromatography (Biotage® system) and then crystallized. Product 1,1,3,3-tetramethyl-2,3,4,5-tetrahydro-1H-7,9-diaza-cyclopenta[a]naphthalene (~5 g) is obtained.

EXAMPLE V

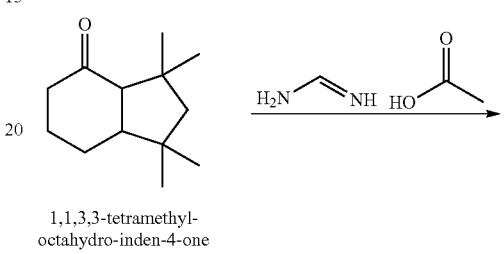

1,1,3,3-tetramethyl-octahydro-inden-4-one

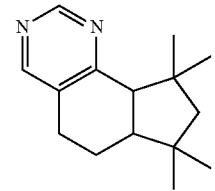

Structure 4

Preparation of 1,1,3,3-Tetramethyl-2,3,3a,4,5,9b-hexahydro-1H-7,9-diaza-cyclopenta[a]naphthalene (Structure 4): 1,1,3,3-Tetramethyl-octahydro-inden-4-one is first prepared by hydrogenating 1,1,3,3-tetramethyl-1,2,3,5,6,7-hexahydro-inden-4-one (prepared as described in U.S. Pat. No. 3,927,083) with Pd/C in alcohol in a Parr Hydrogenator at 25-60° C. and under 500 psi of hydrogen gas. A 100 mL reaction flask is the charged with 1,1,3,3-tetramethyl-octahydro-inden-4-one (10 g, 0.05 mol), formamidine acetate (27 g, 0.26 mol), and butanol (50 mL). The reaction mixture is heated to 130° C. and stirred for 24 hours. The crude mass is washed once with aqueous sulfuric acid (10%, 100 mL) followed by twice with brine (30 mL). Butanol is recovered by roto-evaporation. The crude product is further purified with liquid chromatography (Biotage® system) and then crystallized. Product 1,1,3,3-tetramethyl-2,3,3a,4,5,9b-hexahydro-1H-7,9-diaza-cyclopenta[a]naphthalene (~5 g) is obtained.

EXAMPLE VI

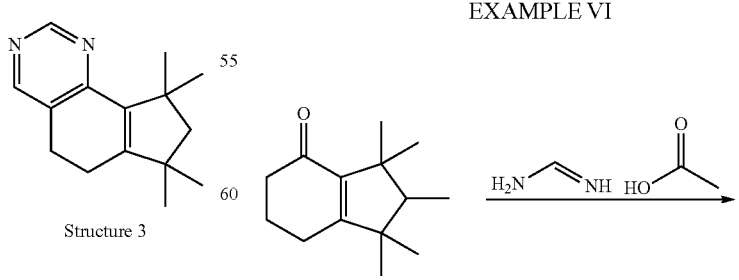

1,1,2,3,3,6-hexamethyl-1,2,3,5,6,7-hexahydro-inden-4-one

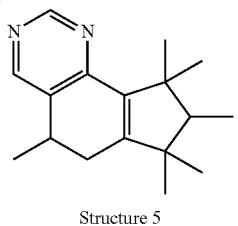

Structure 5

Preparation of 1,1,2,3,3,5-Hexamethyl-2,3,4,5-tetrahydro-1H-7,9-diaza-cyclopenta[a]naphthalene (Structure 5): A 100 mL reaction flask is charged with 1,1,2,3,3,6-hexamethyl-1,2,3,5,6,7-hexahydro-inden-4-one (prepared as described in U.S. Pat. No. 3,927,083) (10 g, 0.045 mol), formamidine acetate (23 g, 0.22 mol), and butanol (50 mL). The reaction mixture is heated to 130° C. and stirred for 24 hours. The crude mass is washed once with aqueous sulfuric acid (10%, 100 mL) followed by twice with brine (30 mL). Butanol is recovered by roto-evaporation. The crude product is further purified with liquid chromatography (Biotage® system) and then crystallized. Product 1,1,2,3,3,5-hexamethyl-2,3,4,5-tetrahydro-1H-7,9-diaza-cyclopenta[a]naphthalene (~5 g) is obtained.

EXAMPLE VII

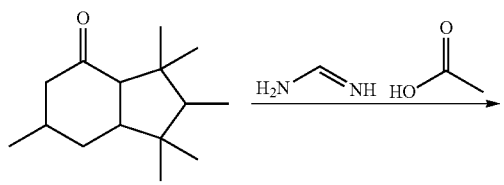

1,1,2,3,3,6-hexamethyl-
octahydro-inden-4-one

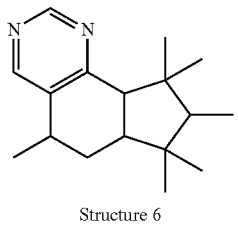

Structure 6

Preparation of 1,1,2,3,3,5-Hexamethyl-2,3,3a,4,5,9b-hexahydro-1H-7,9-diaza-cyclopenta[a]naphthalene (Structure 6): 1,1,2,3,3,6-Hexamethyl-octahydro-inden-4-one is first prepared by hydrogenating 1,1,2,3,3,6-hexamethyl-1,2,3,5,6,7-hexahydro-inden-4-one (prepared as described in U.S. Pat. No. 3,927,083) with Pd/C in alcohol in a Parr Hydrogenator at 25-60° C. and under 500 psi of hydrogen gas. A 100 mL reaction flask is the charged with 1,1,2,3,3,6-hexamethyl-octahydro-inden-4-one (10 g, 0.045 mol), formamidine acetate (23 g, 0.22 mol), and butanol (50 mL). The reaction mixture is heated to 130° C. and stirred for 24 hours. The crude mass is washed once with aqueous sulfuric acid (10%, 100 mL) followed by twice with brine (30 mL). Butanol is recovered by roto-evaporation. The crude product is further purified with liquid chromatography (Biotage® system) and then crystallized. Product 11,1,2,3,3,5-hexamethyl-2,3,3a,4,5,9b-hexahydro-1H-7,9-diaza-cyclopenta[a]naphthalene (~5 g) is obtained.

EXAMPLE VIII

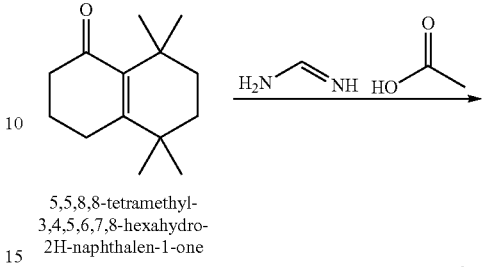

5,5,8,8-tetramethyl-
3,4,5,6,7,8-hexahydro-
2H-naphthalen-1-one

Structure 7

Preparation of 7,7,10,10-Tetramethyl-5,6,7,8,9,10-hexahydro-benzo[h]quinazoline (Structure 7): A 100 mL reaction flask is charged with 5,5,8,8-tetramethyl-3,4,5,6,7,8-hexahydro-2H-naphthalen-1-one (prepared as described in U.S. Pat. Nos. 3,927,083 and 2,912,462) (10 g, 0.048 mol), formamidine acetate (25 g, 0.24 mol), and butanol (50 mL). The reaction mixture is heated to 130° C. and stirred for 24 hours. The crude mass is washed once with aqueous sulfuric acid (10%, 100 mL) followed by twice with brine (30 mL). Butanol is recovered by roto-evaporation. The crude product is further purified with liquid chromatography (Biotage® system) and then crystallized. Product 7,7,10,10-tetramethyl-5,6,7,8,9,10-hexahydro-benzo[h]quinazoline (~5 g) is obtained.

EXAMPLE IX

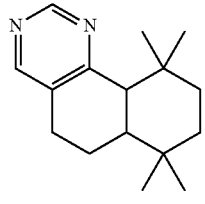

5,5,8,8-tetramethyl-octahydro
-naphthalen-1-one

Structure 8

Preparation of 7,7,10,10-Tetramethyl-5,6,6a,7,8,9,10,10a-octahydro-benzo[h]quinazoline (Structure 8): 5,5,8,8-Tetramethyl-octahydro-naphthalen-1-one is first prepared by hydrogenating 5,5,8,8-tetramethyl-3,4,5,6,7,8-hexahydro-2H-naphthalen-1-one (prepared as described in U.S. Pat.

Nos. 3,927,083 and 2,912,462) with Pd/C in alcohol in a Parr Hydrogenator at 25-60° C. and under 500 psi of hydrogen gas. A 100 mL reaction flask is the charged with 5,5,8,8-tetramethyl-octahydro-naphthalen-1-one (10 g, 0.048 mol), formamidine acetate (25 g, 0.24 mol), and butanol (50 mL). The reaction mixture is heated to 130° C. and stirred for 24 hours. The crude mass is washed once with aqueous sulfuric acid (10%, 100 mL) followed by twice with brine (30 mL). Butanol is recovered by roto-evaporation. The crude product is further purified with liquid chromatography (Biotage® system) and then crystallized. Product 7,7,10,10-tetramethyl-5,6,6a,7,8,9,10,10a-octahydro-benzo[11]quinazoline (~5 g) is obtained.

EXAMPLE X

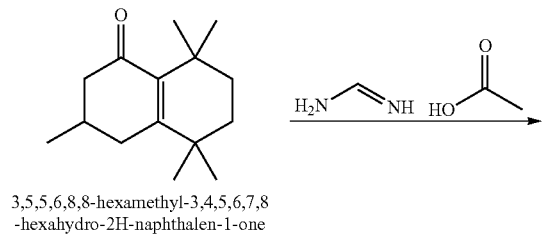

3,5,5,6,8,8-hexamethyl-3,4,5,6,7,8-hexahydro-2H-naphthalen-1-one

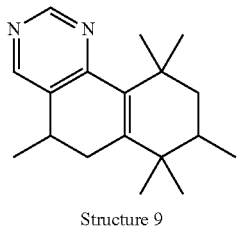

Structure 9

Preparation of 5,7,7,8,10,10-Hexamethyl-5,6,7,8,9,10-hexahydro-benzo[h]quinazoline (Structure 9): A 100 mL reaction flask is charged with 3,5,5,6,8,8-hexamethyl-3,4,5,6,7,8-hexahydro-2H-naphthalen-1-one (prepared as described in U.S. Pat. No. 3,927,083) (10 g, 0.042 mol), formamidine acetate (21 g, 0.2 mol), and butanol (50 mL). The reaction mixture is heated to 130° C. and stirred for 24 hours. The crude mass is washed once with aqueous sulfuric acid (10%, 100 mL) followed by twice with brine (30 mL). Butanol is recovered by roto-evaporation. The crude product is further purified with liquid chromatography (Biotage® system) and then crystallized. Product 5,7,7,8,10,10-hexamethyl-5,6,7,8,9,10-hexahydro-benzo[h]quinazoline (~5 g) is obtained.

EXAMPLE XI

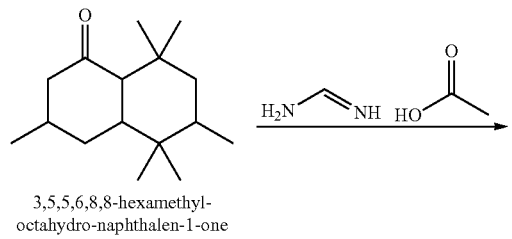

3,5,5,6,8,8-hexamethyl-octahydro-naphthalen-1-one

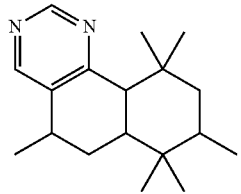

Structure 10

Preparation of 5,7,7,8,10,10-Hexamethyl-5,6,6a,7,8,9,10,10a-octahydro-benzo[h]quinazoline (Structure 10): 3,5,5,6,8,8-Hexamethyl-octahydro-naphthalen-1-one is first prepared by hydrogenating 3,5,5,6,8,8-hexamethyl-3,4,5,6,7,8-hexahydro-2H-naphthalen-1-one (prepared as described in U.S. Pat. No. 3,927,083) with Pd/C in alcohol in a Parr Hydrogenator at 25-60° C. and under 500 psi of hydrogen gas. A 100 mL reaction flask is the charged with 3,5,5,6,8,8-hexamethyl-octahydro-naphthalen-1-one (10 g, 0.042 mol), formamidine acetate (21 g, 0.2 mol), and butanol (50 mL). The reaction mixture is heated to 130° C. and stirred for 24 hours. The crude mass is washed once with aqueous sulfuric acid (10%, 100 mL) followed by twice with brine (30 mL). Butanol is recovered by roto-evaporation. The crude product is further purified with liquid chromatography (Biotage® system) and then crystallized. Product 5,7,7,8,10,10-hexamethyl-5,6,6a,7,8,9,10,10a-octahydro-benzo[h]quinazoline (~5 g) is obtained.

EXAMPLE XII

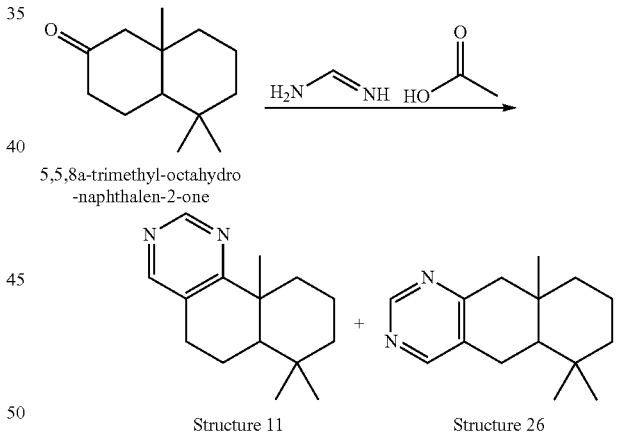

5,5,8a-trimethyl-octahydro-naphthalen-2-one

Structure 11    Structure 26

Preparation of 7,7,10a-Trimethyl-5,6,6a,7,8,9,10,10a-octahydro-benzo[h]quinazoline (Structure 11) and 6,6,9a-Trimethyl-5,5a,6,7,8,9,9a,10-octahydro-benzo[g]quinazoline (Structure 26): A 100 mL reaction flask is charged with 5,5,8a-trimethyl-octahydro-naphthalen-2-one (prepared as described by Strike in Journal of the American Chemical Society, 1964, 86(10), pages: 2044-2050) (10 g, 0.05 mol), formamidine acetate (27 g, 0.26 mol), and butanol (50 mL). The reaction mixture is heated to 130° C. and stirred for 24 hours. The crude mass is washed once with aqueous sulfuric acid (10%, 100 mL) followed by twice with brine (30 mL). Butanol is recovered by roto-evaporation. The crude product is further purified with liquid chromatography (Biotage® system) and then crystallized. A mixture of products 5,7,7,8,10,10-hexamethyl-5,6,7,8,9,10-hexahydro-benzo[h]

quinazoline and 6,6,9a-Trimethyl-5,5a,6,7,8,9,9a,10-octahydro-benzo[g]quinazoline (~5 g) is obtained, which may be separated using techniques known to those having skill in the art. Suitable techniques include chromatography such as high performance liquid chromatography, referred to as HPLC, and particularly silica gel chromatography and gas chromatography trapping known as GC trapping.

EXAMPLE XIII

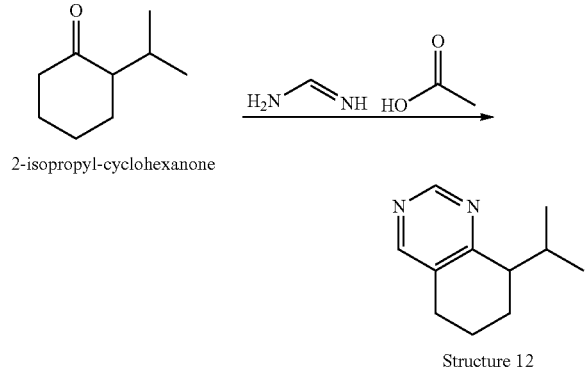

Structure 12

Preparation of 8-Isopropyl-5,6,7,8-tetrahydro-quinazoline (Structure 12): A 100 mL reaction flask is charged with 2-isopropyl-cyclohexanone (10 g, 0.07 mol), formamidine acetate (40 g, 0.4 mol), and butanol (50 mL). The reaction mixture is heated to 130° C. and stirred for 24 hours. The crude mass is washed once with aqueous sulfuric acid (10%, 100 mL) followed by twice with brine (30 mL). Butanol is recovered by roto-evaporation. The crude product is further purified with liquid chromatography (Biotage® system) and then crystallized. Product 8-isopropyl-5,6,7,8-tetrahydro-quinazoline (~5 g) is obtained.

EXAMPLE XIV

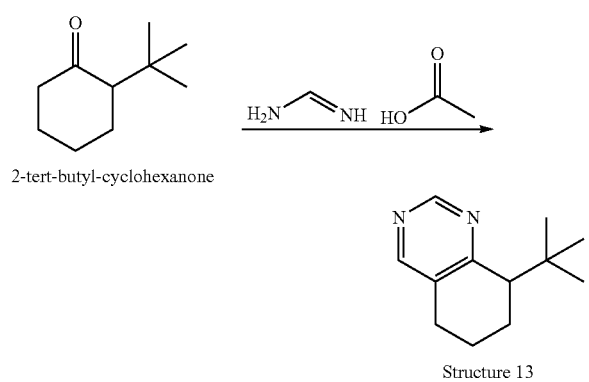

Structure 13

Preparation of 8-tert-Butyl-5,6,7,8-tetrahydro-quinazoline (Structure 13): A 100 mL reaction flask is charged with 2-tert-butyl-cyclohexanone (10 g, 0.07 mol), formamidine acetate (40 g, 0.4 mol), and butanol (50 mL). The reaction mixture is heated to 130° C. and stirred for 24 hours. The crude mass is washed once with aqueous sulfuric acid (10%, 100 mL) followed by twice with brine (30 mL). Butanol is recovered by roto-evaporation. The crude product is further purified with liquid chromatography (Biotage® system) and then crystallized. Product 8-tert-butyl-5,6,7,8-tetrahydro-quinazoline (~5 g) is obtained.

EXAMPLE XV

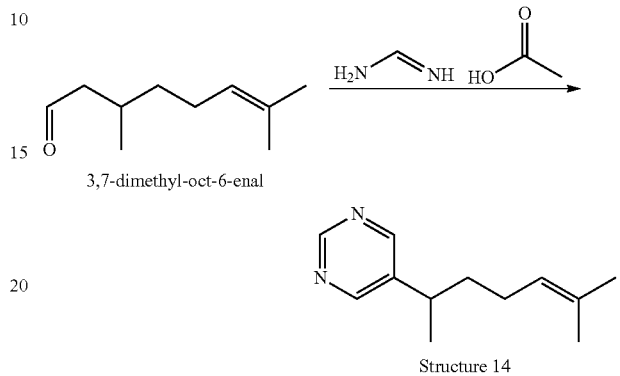

Structure 14

Preparation of 5-(1,5-Dimethyl-hex-4-enyl)-pyrimidine (Structure 14): A 100 mL reaction flask is charged with 3,7-dimethyl-oct-6-enal (Citronellal®) (Commercially available at IFF) (10 g, 0.06 mol), formamidine acetate (31 g, 0.3 mol), and butanol (50 mL). The reaction mixture is heated to 130° C. and stirred for 24 hours. The crude mass is washed once with aqueous sulfuric acid (10%, 100 mL) followed by twice with brine (30 mL). Butanol is recovered by roto-evaporation. The crude product is further purified with liquid chromatography (Biotage® system) and then crystallized. Product 5-(1,5-dimethyl-hex-4-enyl)-pyrimidine (~5 g) is obtained.

EXAMPLE XVI

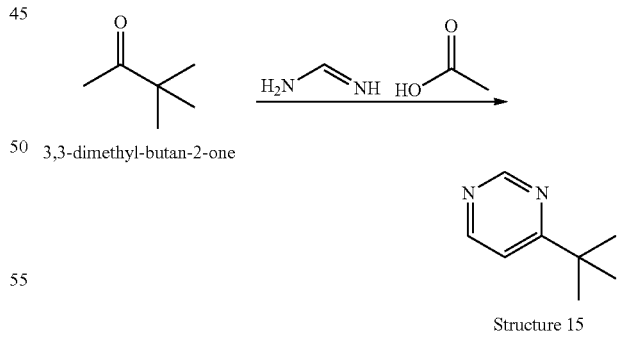

Structure 15

Preparation of 4-tert-Butyl-pyrimidine (Structure 16): A 100 mL reaction flask is charged with 3,3-dimethyl-butan-2-one (10 g, 0.1 mol), formamidine acetate (57 g, 0.5 mol), and butanol (50 mL). The reaction mixture is heated to 130° C. and stirred for 24 hours. The crude mass is washed once with aqueous sulfuric acid (10%, 100 mL) followed by twice with brine (30 mL). Butanol is recovered by roto-evaporation. The crude product is further purified with liquid chromatography

EXAMPLE XVII

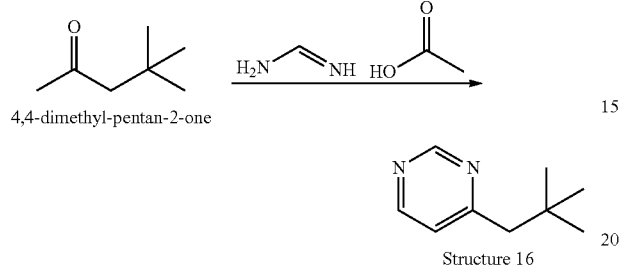

4,4-dimethyl-pentan-2-one

Structure 16

Preparation of 4-(2,2-Dimethyl-propyl)-pyrimidine (Structure 16): A 100 mL reaction flask is charged with 4,4-dimethyl-pentan-2-one (10 g, 0.1 mol), formamidine acetate (57 g, 0.5 mol), and butanol (50 mL). The reaction mixture is heated to 130° C. and stirred for 24 hours. The crude mass is washed once with aqueous sulfuric acid (10%, 100 mL) followed by twice with brine (30 mL). Butanol is recovered by roto-evaporation. The crude product is further purified with liquid chromatography (Biotage® system) and then crystallized. Product 4-(2,2-dimethyl-propyl)-pyrimidine (~5 g) is obtained.

EXAMPLE XVIII

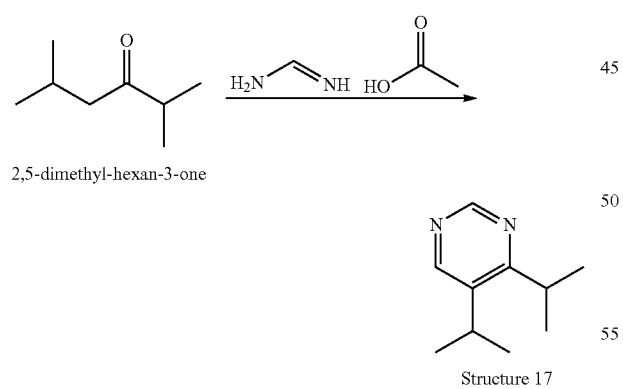

2,5-dimethyl-hexan-3-one

Structure 17

Preparation of 4,5-Diisopropyl-pyrimidine (Structure 17): A 100 mL reaction flask is charged with 2,5-dimethyl-hexan-3-one (10 g, 0.08 mol), formamidine acetate (40 g, 0.4 mol), and butanol (50 mL). The reaction mixture is heated to 130° C. and stirred for 24 hours. The crude mass is washed once with aqueous sulfuric acid (10%, 100 mL) followed by twice with brine (30 mL). Butanol is recovered by roto-evaporation. The crude product is further purified with liquid chromatography (Biotage® system) and then crystallized. Product 4,5-diisopropyl-pyrimidine (~5 g) is obtained.

EXAMPLE XIX

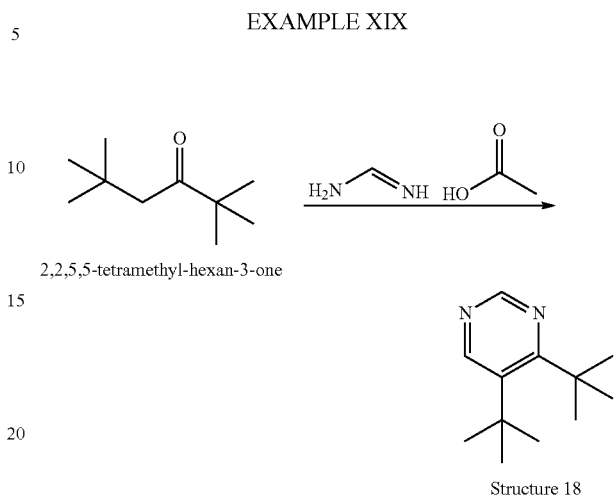

2,2,5,5-tetramethyl-hexan-3-one

Structure 18

Preparation of 4,5-Di-tert-butyl-pyrimidine (Structure 18): A 100 mL reaction flask is charged with 2,2,5,5-tetramethyl-hexan-3-one (10 g, 0.06 mol), formamidine acetate (33 g, 0.3 mol), and butanol (50 mL). The reaction mixture is heated to 130° C. and stirred for 24 hours. The crude mass is washed once with aqueous sulfuric acid (10%, 100 mL) followed by twice with brine (30 mL). Butanol is recovered by roto-evaporation. The crude product is further purified with liquid chromatography (Biotage® system) and then crystallized. Product 4,5-di-tert-butyl-pyrimidine (~5 g) is obtained.

EXAMPLE XX

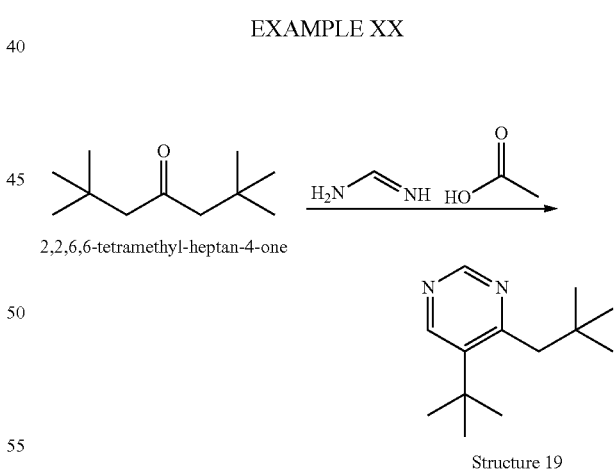

2,2,6,6-tetramethyl-heptan-4-one

Structure 19

Preparation of 5-tert-Butyl-4-(2,2-dimethyl-propyl)-pyrimidine (Structure 19): A 100 mL reaction flask is charged with 2,2,6,6-tetramethyl-heptan-4-one (10 g, 0.06 mol), formamidine acetate (33 g, 0.3 mol), and butanol (50 mL). The reaction mixture is heated to 130° C. and stirred for 24 hours. The crude mass is washed once with aqueous sulfuric acid (10%, 100 mL) followed by twice with brine (30 mL). Butanol is recovered by roto-evaporation. The crude product is further purified with liquid chromatography (Biotage® system) and then crystallized. Product 5-tert-butyl-4-(2,2-dimethyl-propyl)-pyrimidine (~5 g) is obtained.

EXAMPLE XXI

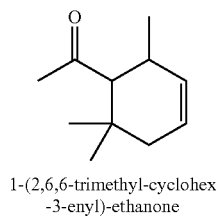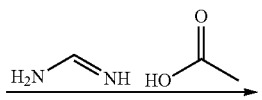

1-(2,6,6-trimethyl-cyclohex-3-enyl)-ethanone

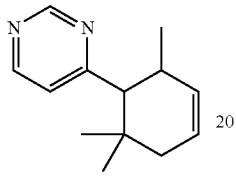

Structure 20

Preparation of 4-(2,6,6-Trimethyl-cyclohex-3-enyl)-pyrimidine (Structure 20): A 100 mL reaction flask is charged with 1-(2,6,6-trimethyl-cyclohex-3-enyl)-ethanone (10 g, 0.06 mol, commercially available at IFF), formamidine acetate (31 g, 0.3 mol), and butanol (50 mL). The reaction mixture is heated to 130° C. and stirred for 24 hours. The crude mass is washed once with aqueous sulfuric acid (10%, 100 mL) followed by twice with brine (30 mL). Butanol is recovered by roto-evaporation. The crude product is further purified with liquid chromatography (Biotage® system) and then crystallized. Product 4-(2,6,6-trimethyl-cyclohex-3-enyl)-pyrimidine (~10 g) is obtained.

EXAMPLE XXII

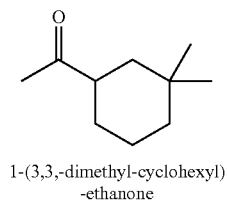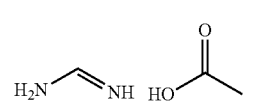

1-(3,3,-dimethyl-cyclohexyl)-ethanone

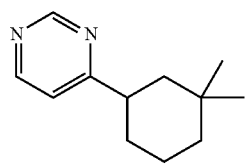

Structure 21

Preparation of 4-(3,3-Dimethyl-cyclohexyl)-pyrimidine (Structure 21): A 100 mL reaction flask is charged with 1-(3,3-dimethyl-cyclohexyl)-ethanone (Herbac®) (10 g, 0.06 mol, commercially available at IFF), formamidine acetate (31 g, 0.3 mol), and butanol (50 mL). The reaction mixture is heated to 130° C. and stirred for 24 hours. The crude mass is washed once with aqueous sulfuric acid (10%, 100 mL) followed by twice with brine (30 mL). Butanol is recovered by roto-evaporation. The crude product is further purified with liquid chromatography (Biotage® system) and then crystallized. Product 4-(3,3-dimethyl-cyclohexyl)-pyrimidine (~10 g) is obtained.

EXAMPLE XXIII

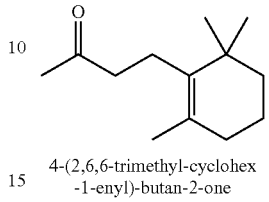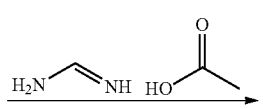

4-(2,6,6-trimethyl-cyclohex-1-enyl)-butan-2-one

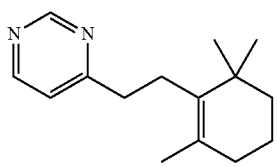

Structure 22

Preparation of 4-[2-(2,6,6-Trimethyl-cyclohex-1-enyl)-ethyl]-pyrimidine (Structure 22): A 100 mL reaction flask is charged with 4-(2,6,6-trimethyl-cyclohex-1-enyl)-butan-2-one (10 g, 0.05 mol, commercially available at IFF), formamidine acetate (26 g, 0.3 mol), and butanol (50 mL). The reaction mixture is heated to 130° C. and stirred for 24 hours. The crude mass is washed once with aqueous sulfuric acid (10%, 100 mL) followed by twice with brine (30 mL). Butanol is recovered by roto-evaporation. The crude product is further purified with liquid chromatography (Biotage® system) and then crystallized. Product 4-[2-(2,6,6-trimethyl-cyclohex-1-enyl)-ethyl]-pyrimidine (~10 g) is obtained.

EXAMPLE XXIV

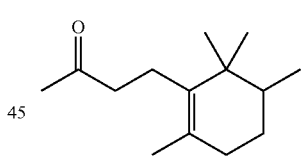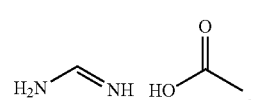

4-(2,5,6,6-tetramethyl-cyclohex-1-enyl)-butan-2-one

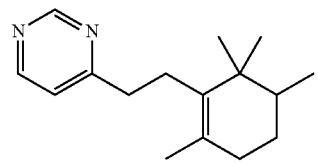

Structure 23

Preparation of 4-[2-(2,5,6,6-Tetramethyl-cyclohex-1-enyl)-ethyl]-pyrimidine (Structure 23): A 100 mL reaction flask is charged with 4-(2,5,6,6-tetramethyl-cyclohex-1-enyl)-butan-2-one (10 g, 0.05 mol, commercially available at IFF), formamidine acetate (26 g, 0.3 mol), and butanol (50 mL). The reaction mixture is heated to 130° C. and stirred for 24 hours. The crude mass is washed once with aqueous sulfuric acid (10%, 100 mL) followed by twice with brine (30 mL). Butanol is recovered by roto-evaporation. The crude product is further purified with liquid chromatography (Biotage® system) and then crystallized. Product 4-[2-(2,5,6,6-tetramethyl-cyclohex-1-enyl)-ethyl]-pyrimidine (~10 g) is obtained.

EXAMPLE XXV

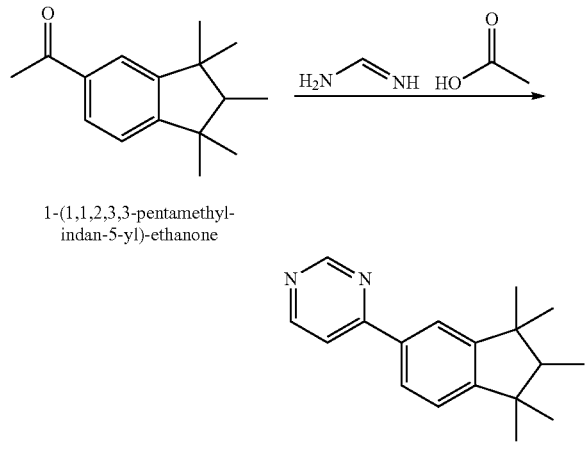

1-(1,1,2,3,3-pentamethyl-indan-5-yl)-ethanone

Structure 24

Preparation of 4-(1,1,2,3,3-Pentamethyl-indan-5-yl)-pyrimidine (Structure 24): A 5 L reaction vessel was charged with 1-(1,1,2,3,3-pentamethyl-indan-5-yl)-ethanone (460 g, 2.0 mol) (commercially available at IFF), formamidine acetate (675 g, 6.4 mol), and butanol (1.0 L). The reaction mixture was heated to 120° C. for 10 hours and then cooled to 25° C. The reaction mixture was washed twice with brine (1 L) and purified by vacuum distillation to afford 4-(1,1,2,3,3-pentamethyl-indan-5-yl)-pyrimidine (200 g) having a boiling point of 153° C. at a pressure of 2.0 mmHg $^1$H NMR (CDCl$_3$, 500 MHz): 9.25 ppm (d, 1H, J=1.28 Hz), 8.71 ppm (d, 1H, J=5.40 Hz), 7.88-7.93 ppm (m, 2H), 7.69 (d, 1H, J=5.40 Hz, of d, J=1.40 Hz), 7.28 ppm (d, 1H, J=7.90 Hz, of d, J=0.40 Hz), 1.92 ppm (q, 1H, J=7.36 Hz), 1.35 ppm (s, 3H), 1.31 ppm (s, 3H), 1.13 ppm (s, 3H), 1.11 ppm (s, 3H), 1.02 ppm (d, 3H, J=7.36 Hz).

4-(1,1,2,3,3-Pentamethyl-indan-5-yl)-pyrimidine was described as having weak floral note.

EXAMPLE XXVI

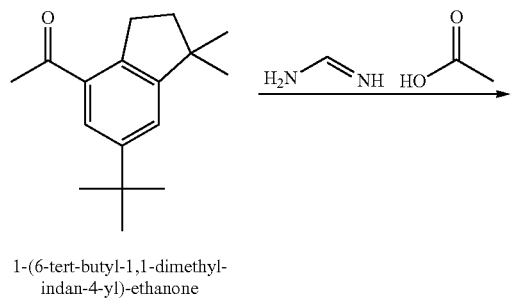

1-(6-tert-butyl-1,1-dimethyl-indan-4-yl)-ethanone

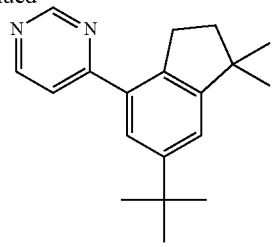

Structure 25

Preparation of 4-(6-tert-Butyl-1,1-dimethyl-indan-4-yl)-pyrimidine (Structure 25): A 5 L reaction vessel was charged with 1-(6-tert-butyl-1,1-dimethyl-indan-4-yl)-ethanone (300 g, 1.2 mol) (commercially available at IFF), formamidine acetate (639 g, 6.1 mol), and butanol (1.0 L). The reaction mixture was heated to 125° C. for 10 hours and then cooled to 25° C. The reaction mixture was washed twice with brine (1 L) and purified by vacuum distillation to afford 4-(6-tert-butyl-1,1-dimethyl-indan-4-yl)-pyrimidine (200 g) having a boiling point of 180° C. at a pressure of 0.5 mmHg $^1$H NMR (CDCl$_3$, 500 MHz): 9.28 ppm (d, 1H, J=1.28 Hz), 8.74 ppm (d, 1H, J=5.32 Hz), 7.65 ppm (d, 1H, J=1.84 Hz), 7.57 ppm (d, 1H, J=5.32 Hz, of d, J=1.44 Hz), 7.31 ppm (d, 1H, J=1.80 Hz), 3.11 ppm (t, 2H, J=7.14 Hz), 1.95 ppm (t, 2H, J=7.14 Hz), 1.38 ppm (s, 9H), 1.31 ppm (s, 6H).

4-(6-tert-Butyl-1,1-dimethyl-indan-4-yl)-pyrimidine was described as having weak fatty note.

EXAMPLE XXVII

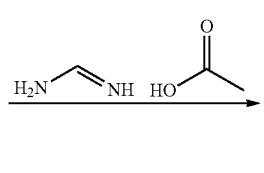

1,4a-dimethyl-4,4a,5,6,7,8-hexahydro-3H-naphthalen-2-one

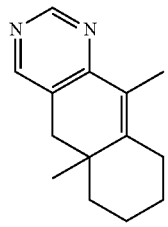

Structure 27

Preparation of 5a,10-Dimethyl-5,5a,6,7,8,9-hexahydro-benzo[g]quinazoline (Structure 27): A 100 mL reaction flask is charged with 1,4a-dimethyl-4,4-a,5,6,7,8-hexahydro-3H-naphthalen-2-one (prepared as described by Sjoebers in Acta Chemica Scand., 1990, 44(10), pages: 1036-1041) (10 g, 0.05 mol), formamidine acetate (27 g, 0.26 mol), and butanol (50 mL). The reaction mixture is heated to 130° C. and stirred for 24 hours. The crude mass is washed once with aqueous sulfuric acid (10%, 100 mL) followed by twice with brine (30 mL). Butanol is recovered by roto-evaporation. The crude product is further purified with liquid chromatography (Biotage® system) and then crystallized. Product 5a,10-dimethyl-5,5a,6,7,8,9-hexahydro-benzo[g]quinazoline (~5 g) is obtained.

EXAMPLE XXVIII

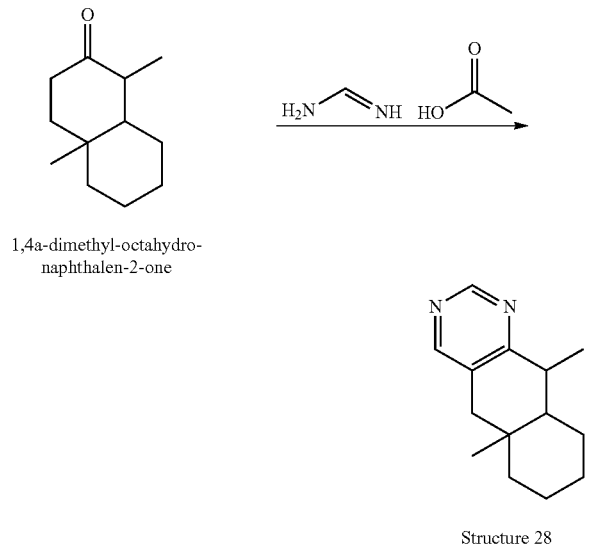

1,4a-dimethyl-octahydro-naphthalen-2-one

Structure 28

Preparation of 5a,10-Dimethyl-5,5a,6,7,8,9,9a,10-octahydro-benzo[g]quinazoline (Structure 28): 1,4a-Dimethyl-octahydro-naphthalen-2-one is first prepared by hydrogenating 1,4a-dimethyl-4,4-a,5,6,7,8-hexahydro-3H-naphthalen-2-one (prepared as described by Sjoebers in Acta Chemica Scand., 1990, 44(10), pages: 1036-1041) with Pd/C in alcohol in a Parr Hydrogenator at 25-60° C. and under 500 psi of hydrogen gas. A 100 mL reaction flask is charged with 1,4a-dimethyl-octahydro-naphthalen-2-one (10 g, 0.05 mol), formamidine acetate (27 g, 0.26 mol), and butanol (50 mL). The reaction mixture is heated to 130° C. and stirred for 24 hours. The crude mass is washed once with aqueous sulfuric acid (10%, 100 mL) followed by twice with brine (30 mL). Butanol is recovered by roto-evaporation. The crude product is further purified with liquid chromatography (Biotage® system) and then crystallized. Product 5a,10-dimethyl-5,5a, 6,7,8,9,9a,10-octahydro-benzo[g]quinazoline (~5 g) is obtained.

EXAMPLE XXIX

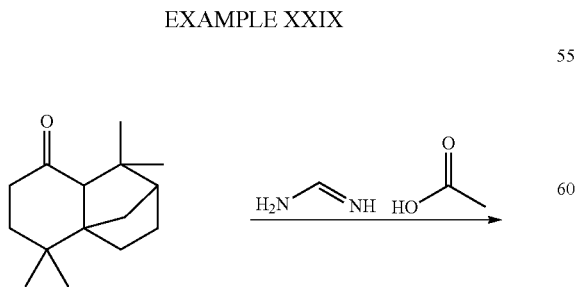

1,1,5,5-tetramethyl-hexahydro-2,4a-methano-naphthalen-8-one

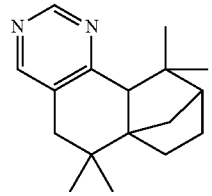

Structure 29

Preparation of 6,6,10,10-Tetramethyl-5,7,8,9,10,10a-hexahydro-6H-6a,9-methanobenzo[H]quinazoline (Structure IV): A 5 L reaction vessel was charged with 1,1,5,5-tetramethyl-hexahydro-2,4-a-methano-naphthalen-8-one (440 g, 2.0 mol) (commercially available at IFF), formamidine acetate (1040 g, 10.0 mol) and butanol (2 L). The reaction mixture was heated to 120° C. for 10 hours and then cooled to 25° C. The reaction mixture was washed twice with brine (1 L) and purified by vacuum distillation to afford crude product 6,6,10,10-tetramethyl-5,7,8,9,10,10a-hexahydro-6H-6a,9-methanobenzo[H]quinazoline (430 g) having a boiling point of 159° C. at a pressure of 1.0 mmHg. Further recrystallization from ethanol afforded 6,6,10,10-tetramethyl-5,7,8,9,10,10a-hexahydro-6H-6a,9-methanobenzo[H] quinazoline (95% purity) (125 g) with a melting point of 44-45° C.

$^1$H NMR (CDCl$_3$, 500 MHz): 8.97 ppm (d, 1H, J=0.60 Hz), 8.34 ppm (s, 1H), 2.81 ppm (d, 1H, J=16.14 Hz), 2.45 ppm (s, 1H), 2.30 ppm (d, 1H, J=16.11 Hz), 1.90-1.97 ppm (m, 1H), 1.76-1.77 ppm (m, 1H), 1.71 ppm (d, 1H, J=3.95 Hz, of t, J=12.22 Hz), 1.61-1.66 ppm (d, 1H, J=9.45 Hz, of m), 1.51-1.58 ppm (m, 1H), 1.39 ppm (s, 3H), 1.28 ppm (d, 1H, J=9.95 Hz, of t, J=1.68 Hz), 1.16-1.23 ppm (m, 1H), 1.09 ppm (s, 3H), 0.74 ppm (s, 3H), 0.67 ppm (s, 3H).

6,6,10,10-Tetramethyl-5,7,8,9,10,10a-hexahydro-6H-6a, 9-methanobenzo[H]quinazoline was described as having musky, woody, and ambery notes.

EXAMPLE XXX

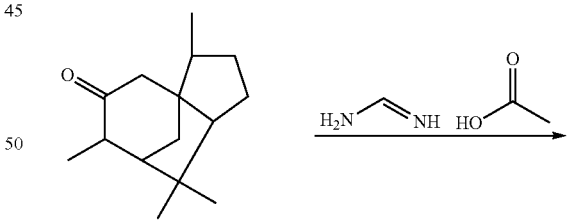

3,6,8,8-tetramethyl-hexahydro-3a,7-methano-azulen-5-one

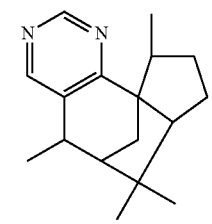

Structure 30

Preparation of 5,7,7,10-Tetramethyl-6,7,7a,8,9,10-hexahydro-5H-6,10a-methanoazuleno[5,4-d]pyrimidine (Structure 30): A 100 mL reaction flask is charged with 3,6,8,8-tetramethyl-hexahydro-3a,7-methano-azulen-5-one (prepared as described in U.S. Pat. No. 3,887,622) (10 g, 0.045 mol), formamidine acetate (21 g, 0.2 mol), and butanol (50 mL). The reaction mixture is heated to 130° C. and stirred for 24 hours. The crude mass is washed once with aqueous sulfuric acid (10%, 100 mL) followed by twice with brine (30 mL). Butanol is recovered by roto-evaporation. The crude product is further purified with liquid chromatography (Biotage® system) and then crystallized. Product 5,7,7,10-tetramethyl-6,7,7a, 8,9,10-hexahydro-5H-6,10a-methanoazuleno[5,4-d]pyrimidine (~5 g) is obtained.

EXAMPLE XXXI

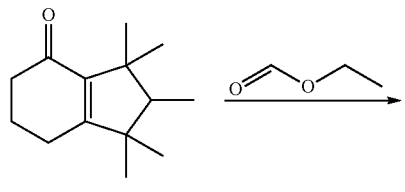

Cashmeran

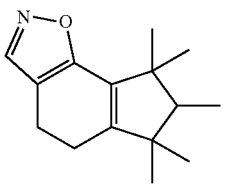

1,1,2,3,3-pentamethyl-4-oxo-2,3,4,5,6,7-hexahydro-1H-indene-5-carbaldehyde

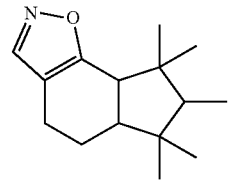

Structure 31

Preparation of 5,6,7,8-Tetrahydro-6,6,7,8,8-pentamethyl-4H-indeno[5,4-D]isoxazole (Structure 31): A 2 L reaction flask was charged with sodium hydride (NaH) (40 g) in dimethoxyethane (DME) (CH$_3$OCH$_2$CH$_2$OCH$_3$) (1.39 Kg) and a mixture of Cashmeran™ (520 g) and ethyl formate (185 g) at room temperature. The mixture was stirred for 8 hours to provide 1,1,2,3,3-pentamethyl-4-oxo-2,3,4,5,6,7-hexahydro-1H-indene-5-carbaldehyde. Dimethylformamide (DMF) (300 mL) and hydroxylamine hydrochloride (NH$_2$OH*HCl) (174 g) were then added and the temperature was heated to and maintained at 130° C. for 8 hours. Water was then added and the organic layer was extracted by toluene and washed once with water. Toluene was distilled off using a Rotovap to provide crude product 5,6,7,8-tetrahydro-6,6,7,8,8-pentamethyl-4H-indeno[5,4-D]isoxazole (260 g), which was then recrystallized to afford a pure product with a melting point of 80.96° C.

$^1$H NMR (CDCl$_3$, 500 MHz): 8.01 ppm (s, 1H), 2.68-2.73 ppm (m, 2H), 2.28-2.43 ppm (m, 2H), 1.75 ppm (q, 1H, J=7.40 Hz), 1.31 ppm (s, 3H), 1.09 ppm (s, 3H), 1.07 ppm (s, 3H), 0.93 ppm (s, 3H), 0.93 ppm (d, 3H, J=7.40 Hz).

5,6,7,8-Tetrahydro-6,6,7,8,8-pentamethyl-4H-indeno[5,4-D]isoxazole was described as having cashmeran, slightly musky, geranium, and hint of ambery notes.

EXAMPLE XXXII

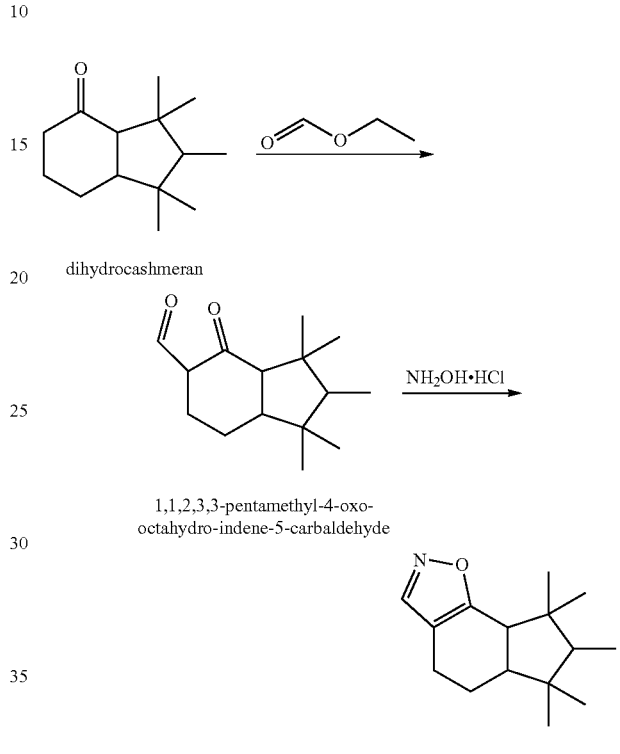

Structure 32

Preparation of 5,5a,6,7,8,8a-Hexahydro-6,6,7,8,8-pentamethyl-4H-indeno[5,4-D]isoxazole (Structure 32): A 2 L reaction flask was charged with sodium hydride (24 g) in DME (867 g) and a mixture of dihydrocashmeran (208 g, prepared as above in EXAMPLE II) and ethyl formate (111 g) at room temperature. The mixture was stirred for 8 hours to provide 1,1,2,3,3-pentamethyl-4-oxo-octahydro-indene-5-carbaldehyde. Tetrahydrofuran (THF) (20 mL), ethanol (CH$_3$CH$_2$OH) (200 mL), hydroxylamine hydrochloride (70 g), and acetic acid (CH$_3$COOH) (200 mL) were then added and the temperature was heated to and maintained at 75° C. for 8 hours. Water was then added and the organic layer was extracted by toluene and washed once with water. Toluene was distilled off using a Rotovap to provide crude product 5,5a,6,7,8,8a-hexahydro-6,6,7,8,8-pentamethyl-4H-indeno[5,4-D]isoxazole (186 g), which was then recrystallized to afford a pure product with a melting point of 82.35° C.

$^1$H NMR (CDCl$_3$, 400 MHz): 8.03 ppm (s, 1H), 2.57-2.64 ppm (m, 2H), 2.40-2.50 ppm (m, 1H), 1.88-1.94 ppm (m, 1H), 1.61 ppm (d, 1H, J=2.24 Hz, of t, J=12.42 Hz), 1.43 ppm (q, 1H, J=7.53 Hz), 1.30-1.39 ppm (m, 1H), 1.19 ppm (s, 3H), 1.00 ppm (s, 3H), 0.94 ppm (s, 3H), 0.84 ppm (d, 3H, J=7.52 Hz), 0.70 ppm (s, 3H).

5,5a,6,7,8,8a-Hexahydro-6,6,7,8,8-pentamethyl-4H-indeno[5,4-D]isoxazole was described as having woody, earthy, green, patchouli, cashmeran, moldy, cucumber, aldehydic, moss and ambery notes.

EXAMPLE XXXIII

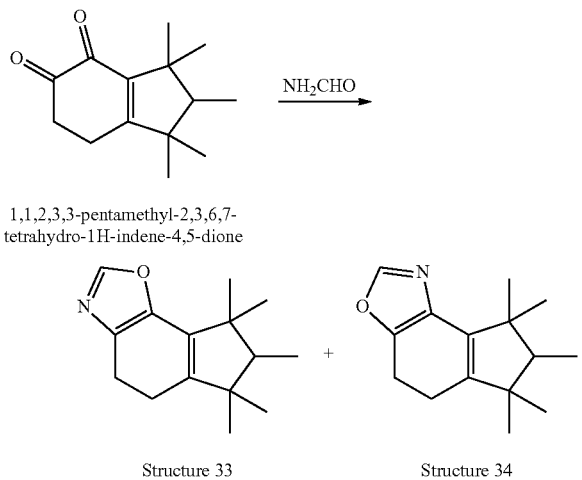

1,1,2,3,3-pentamethyl-2,3,6,7-
tetrahydro-1H-indene-4,5-dione

Structure 33    Structure 34

Preparation of 6,6,7,8,8-Pentamethyl-5,6,7,8-tetrahydro-4H-1-oxa-3-aza-as-indacene (Structure 33) and 6,6,7,8,8-Pentamethyl-5,6,7,8-tetrahydro-4H-indeno[4,5-d]oxazole (Structure 34): 1,1,2,3,3-Pentamethyl-2,3,6,7-tetrahydro-1H-indene-4,5-dione is first prepared with 1,1,2,3,3-pentamethyl-1,2,3,5,6,7-hexahydro-inden-4-one (Cashmeran®) (commercially available at IFF) via oxidation with (2,2,6,6-tetramethylpiperidin-1-yl)oxidanyl (TEMPO) (prepared as described by Barton in Tetrahedron Letters, 1984, 25(6), pages: 603-606). A 100 mL reaction flask is charged with 1,1,2,3,3-pentamethyl-2,3,6,7-tetrahydro-1H-indene-4,5-dione (10 g, 0.04 mol) and formamide ($NH_2CHO$) (50 mL). The reaction mixture is heated to 200° C. and stirred for 24 hours. The crude mass is diluted with toluene (50 mL) and then washed once with aqueous sodium carbonate (10%, 100 mL) followed by twice with brine (30 mL). Toluene is recovered by roto-evaporation. The crude product is further purified with liquid chromatography (Biotage® system) and then crystallized. Product of a mixture of 6,6,7,8,8-pentamethyl-5,6,7,8-tetrahydro-4H-1-oxa-3-aza-as-indacene and 6,6,7,8,8-pentamethyl-5,6,7,8-tetrahydro-4H-indeno[4,5-d]oxazole (~10 g) is obtained.

EXAMPLE XXXIV

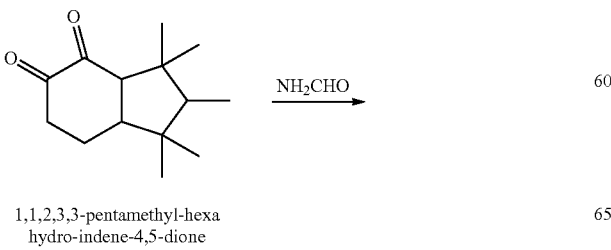

1,1,2,3,3-pentamethyl-hexa
hydro-indene-4,5-dione

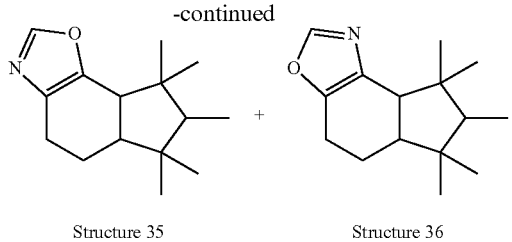

Structure 35    Structure 36

Preparation of 6,6,7,8,8-Pentamethyl-5,5a,6,7,8,8a-hexahydro-4H-1-oxa-3-aza-as-indacene (Structure 35) and 6,6,7,8,8-Pentamethyl-5,5a,6,7,8,8a-hexahydro-4H-indeno[4,5-d]oxazole (Structure 36): 1,1,2,3,3-Pentamethyl-octahydro-inden-4-one is first prepared by the hydrogenation of 1,1,2,3,3-pentamethyl-1,2,3,5,6,7-hexahydro-inden-4-one (Cashmeran®) (commercially available at IFF). 1,1,2,3,3-Pentamethyl-hexahydro-indene-4,5-dione is subsequently prepared with 1,1,2,3,3-pentamethyl-octahydro-inden-4-one (prepared as described by Barton in Tetrahedron Letters, 1984, 25(6), pages: 603-606). A 100 mL reaction flask is charged with 1,1,2,3,3-pentamethyl-hexahydro-indene-4,5-dione (10 g, 0.04 mol) and formamide (50 mL). The reaction mixture is heated to 200° C. and stirred for 24 hours. The crude mass is diluted with toluene (50 mL) and then washed once with aqueous sodium carbonate (10%, 100 mL) followed by twice with brine (30 mL). Toluene is recovered by roto-evaporation. The crude product is further purified with liquid chromatography (Biotage® system) and then crystallized. Product of a mixture of 6,6,7,8,8-pentamethyl-5,5a,6,7,8,8a-hexahydro-4H-1-oxa-3-aza-as-indacene and 6,6,7,8,8-pentamethyl-5,5a,6,7,8,8a-hexahydro-4H-indeno[4,5-d]oxazole (~10 g) is obtained.

EXAMPLE XXXV

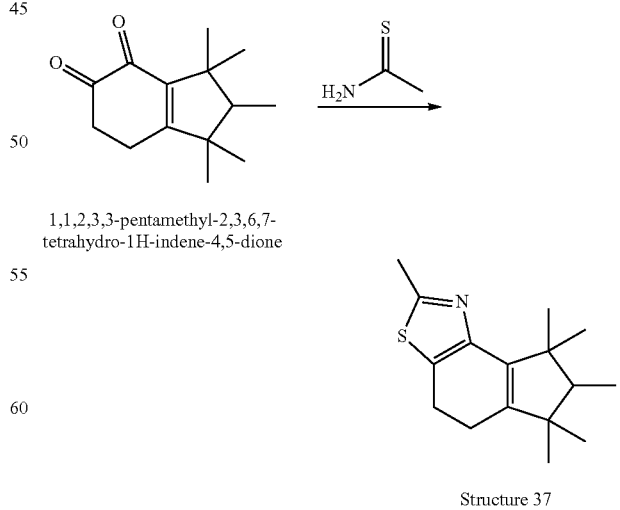

1,1,2,3,3-pentamethyl-2,3,6,7-
tetrahydro-1H-indene-4,5-dione

Structure 37

Preparation of 2,6,6,7,8,8-Hexamethyl-5,6,7,8-tetrahydro-4H-3-thia-1-aza-as-indacene (Structure 37): 1,1,2,3,3-

Pentamethyl-2,3,6,7-tetrahydro-1H-indene-4,5-dione is first prepared with 1,1,2,3,3-pentamethyl-1,2,3,5,6,7-hexahydro-inden-4-one (Cashmeran®) (commercially available at IFF) via oxidation with (2,2,6,6-tetramethylpiperidin-1-yl)oxidanyl (TEMPO) (prepared as described by Barton in Tetrahedron Letters, 1984, 25(6), pages: 603-606). A 100 mL reaction flask is charged with 1,1,2,3,3-pentamethyl-2,3,6,7-tetrahydro-1H-indene-4,5-dione (10 g, 0.04 mol), thioacetamide (CH$_3$CSNH$_2$) (3.5 g, 0.04 mol), and diglyme (50 mL). The reaction mixture is heated to 130° C. and stirred for 24 hours. The crude mass is washed once with aqueous sodium carbonate (10%, 100 mL) followed by twice with brine (30 mL). Diglyme is recovered by roto-evaporation. The crude product is further purified with liquid chromatography (Biotage® system) and then crystallized. Product 2,6,6,7,8,8-hexamethyl-5,6,7,8-tetrahydro-4H-3-thia-1-aza-as-indacene (~10 g) is obtained.

EXAMPLE XXXVI

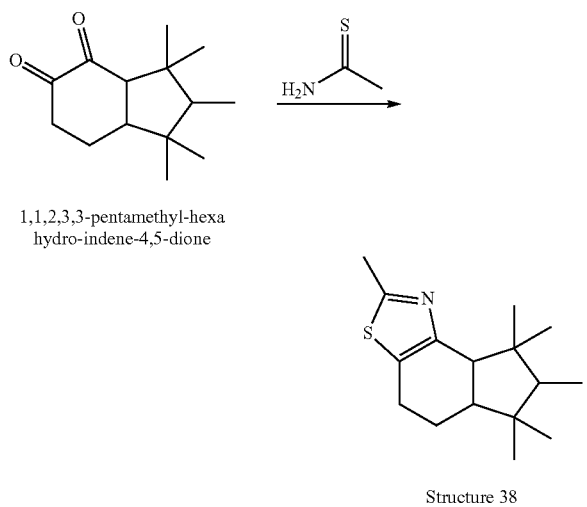

Structure 38

Preparation of 2,6,6,7,8,8-Hexamethyl-5,5a,6,7,8,8a-hexahydro-4H-3-thia-1-aza-as-indacene (Structure 38): 1,1,2,3,3-Pentamethyl-octahydro-inden-4-one is first prepared by the hydrogenation of 1,1,2,3,3-pentamethyl-1,2,3,5,6,7-hexahydro-inden-4-one (Cashmeran®) (commercially available at IFF). 1,1,2,3,3-Pentamethyl-hexahydro-indene-4,5-dione is subsequently prepared with 1,1,2,3,3-pentamethyl-octahydro-inden-4-one (prepared as described by Barton in Tetrahedron Letters, 1984, 25(6), pages: 603-606). A 100 mL reaction flask is charged with 1,1,2,3,3-pentamethyl-hexahydro-indene-4,5-dione (10 g, 0.04 mol), thioacetamide (3.5 g, 0.04 mol), and diglyme (50 mL). The reaction mixture is heated to 130° C. and stirred for 24 hours. The crude mass is washed once with aqueous sodium carbonate (10%, 100 mL) followed by twice with brine (30 mL). Diglyme is recovered by roto-evaporation. The crude product is further purified with liquid chromatography (Biotage® system) and then crystallized. Product 2,6,6,7,8,8-hexamethyl-5,5a,6,7,8,8a-hexahydro-4H-3-thia-1-aza-as-indacene (~10 g) is obtained.

EXAMPLE XXXVII

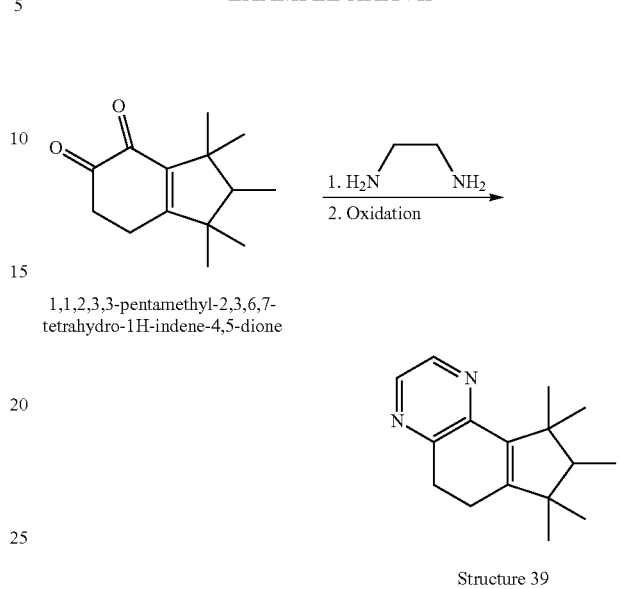

Structure 39

Preparation of 7,7,8,9,9-Pentamethyl-5,7,8,9-tetrahydro-6H-cyclopenta[f]quinoxaline (Structure 39): 1,1,2,3,3-Pentamethyl-2,3,6,7-tetrahydro-1H-indene-4,5-dione is first prepared with 1,1,2,3,3-pentamethyl-1,2,3,5,6,7-hexahydro-inden-4-one (Cashmeran®) (commercially available at IFF) via oxidation with (2,2,6,6-tetramethylpiperidin-1-yl)oxidanyl (TEMPO) (prepared as described by Barton in Tetrahedron Letters, 1984, 25(6), pages: 603-606). A 100 mL reaction flask is charged with 1,1,2,3,3-pentamethyl-2,3,6,7-tetrahydro-1H-indene-4,5-dione (10 g, 0.04 mol), ethylene diamine (NH$_2$CH$_2$CH$_2$NH$_2$) (2.5 g, 0.04 mol), and diglyme (50 mL). The reaction mixture is heated to 130° C. and stirred for 24 hours. The reaction mixture is then cooled to 25° C. and further oxidized with 2,3-dichloro-5,6-dicyano-1,4-benzoquinone (10 g, 0.045 mol) for another 8 hours. The crude mass is washed once with aqueous sodium carbonate (10%, 100 mL) followed by twice with brine (30 mL). Diglyme is recovered by roto-evaporation. The crude product is further purified with liquid chromatography (Biotage® system) and then crystallized. Product 7,7,8,9,9-pentamethyl-5,7,8,9-tetrahydro-6H-cyclopenta[f]quinoxaline (~10 g) is obtained.

EXAMPLE XXXVIII

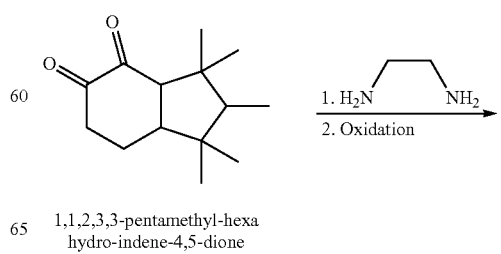

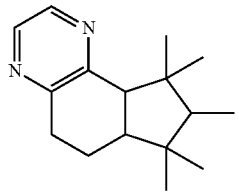

Structure 40

Preparation of 7,7,8,9,9-Pentamethyl-5,6a,7,8,9,9a-hexahydro-6H-cyclopenta[f]quinoxaline (Structure 40): 1,1,2,3,3-Pentamethyl-octahydro-inden-4-one is first prepared by the hydrogenation of 1,1,2,3,3-pentamethyl-1,2,3,5,6,7-hexahydro-inden-4-one (Cashmeran®) (commercially available at IFF). 1,1,2,3,3-Pentamethyl-hexahydro-indene-4,5-dione is subsequently prepared with 1,1,2,3,3-pentamethyl-octahydro-inden-4-one (prepared as described by Barton in Tetrahedron Letters, 1984, 25(6), pages: 603-606). A 100 mL reaction flask is charged with 1,1,2,3,3-pentamethyl-hexahydro-indene-4,5-dione (10 g, 0.04 mol), ethylene diamine ($NH_2CH_2CH_2NH_2$) (2.5 g, 0.04 mol), and diglyme (50 mL). The reaction mixture is heated to 130° C. and stirred for 24 hours. The reaction mixture is then cooled to 25° C. and further oxidized with 2,3-dichloro-5,6-dicyano-1,4-benzoquinone (10 g, 0.045 mol) for another 8 hours. The crude mass is washed once with aqueous sodium carbonate (10%, 100 mL) followed by twice with brine (30 mL). Diglyme is recovered by roto-evaporation. The crude product is further purified with liquid chromatography (Biotage® system) and then crystallized. Product 7,7,8,9,9-pentamethyl-5,6a,7,8,9,9a-hexahydro-6H-cyclopenta[f]quinoxaline (~10 g) is obtained.

EXAMPLE XXXIX

The fragrance formulas exemplified as follows demonstrated that the addition of 1,1,2,3,3-Pentamethyl-2,3,3a,4,5,9b-hexahydro-1H-7,9-diaza-cyclopenta[a]naphthalene (Structure 2) containing a 40:60 cis/trans isomeric mixture provided a musky character to the fragrance formula.

| Ingredient | Parts (g) | Parts (g) |
|---|---|---|
| Kharismal ™ | 175 | 175 |
| Ethylene Brassylate | 50 | 50 |
| Dipropylene Glycol | 34 | 34 |
| Iso Gamma Super ™ | 30 | 30 |
| Hydroxy Citronellal Pure | 15 | 15 |
| Indasan | 10 | 10 |
| Amberiff 20% IPM | 10 | 10 |
| L-Citronellol | 8 | 8 |
| Beta Ionone Extra | 5 | 5 |
| Linalyl Acetate | 5 | 5 |
| Ambrettolide | 3 | 3 |
| Geraniol 980 | 3 | 3 |
| Healingwood ™ | 1 | 1 |
| Amber Xtreme ™ 1% DPG | 1 | 1 |
| Structure 2 | 10 | — |
| DPG | — | 10 |
| Total | 360 | 360 |

The above fragrance formulas had floral and woody characters. The addition of 1,1,2,3,3-pentamethyl-2,3,3a,4,5,9b-hexahydro-1H-7,9-diaza-cyclopenta[a]naphthalene (Structure 2) intensified the floral and woody notes and provided a musky undertone.

EXAMPLE XL

Fragrance formulation containing 1,1,2,3,3-pentamethyl-2,3,3a,4,5,9b-hexahydro-1H-7,9-diaza-cyclopenta[a]naphthalene (Structure 2):

| Ingredient | Parts (g) |
|---|---|
| Santaliff ™ | 24 |
| Phenoxanol ™ | 32 |
| Coumarin | 28 |
| Cyclamal Extra | 1 |
| Eth Vanillin | 7 |
| Geraniol 980 Pure | 1 |
| Hedione ™ | 60 |
| Amy Cinnamic Aldehyde | 60 |
| Heliotropine | 17 |
| Hexyl Cinnamic Ald | 16 |
| Beta Ionone Extra | 6 |
| Iso E Super ™ | 70 |
| Lyral ™ | 16 |
| lillial ™ | 160 |
| Lilianth | 20 |
| Methyl Ionone Gamma A | 73 |
| Veramoss | 2 |
| Peru Balsam Oil India | 3 |
| Prenyl Acetate | 1 |
| Methyl Cedryl Ketone | 40 |
| Methyl Phenyl Acetate | 1 |
| Aubepine | 4 |
| Benzoin | 10 |
| Cedrol Tex | 3 |
| Citronellol Extra | 3 |
| Geraniol Coeur | 4 |
| Methyl Cinnamate | 3 |
| Styrax Alva Ess | 2 |
| Vanillin ex Lignin | 12 |
| Cananga Java Native | 5 |
| Structure 2 | 20 |
| Total | 704 |

1,1,2,3,3-Pentamethyl-2,3,3a,4,5,9b-hexahydro-1H-7,9-diaza-cyclopenta[a]naphthalene (Structure 2) imparted diffusive floral and soft powdery characters to a fragrance formula.

EXAMPLE XLI

The fragrance formulas exemplified as follows demonstrated that the addition of 6,6,10,10-tetramethyl-5,7,8,9,10,10a-hexahydro-6H-6a, 9-methanobenzo[H]quinazoline (Structure 29) provided floral odor character with woody and musky undertones.

| Ingredient | Parts (g) | Parts (g) |
|---|---|---|
| Triplal BHT | 20 | 20 |
| Aldehyde C11 Ulenic | 13 | 13 |
| Aldehyde C12 MNA | 10 | 10 |
| Iso Gamma Super ™ | 170 | 170 |
| Hydroxy Citronellal Pure | 10 | 10 |
| Bacdanol ™ BHT | 10 | 10 |
| Benz Acetone | 25 | 25 |
| Benz Salicylate | 50 | 50 |
| Citronellol 950 | 15 | 15 |
| Cyclacet | 20 | 20 |
| Cyclaprop | 20 | 20 |
| Damascone delta | 2 | 2 |
| Dihydro myrcenol | 60 | 60 |
| Eugenol Natural | 10 | 10 |
| Galaxolide 50 ™ | 140 | 140 |
| Hexyl cinnamic ald | 35 | 35 |

-continued

| Ingredient | Parts (g) | Parts (g) |
|---|---|---|
| Hexyl Salicylate | 35 | 35 |
| Iso bornyl acetate | 40 | 40 |
| Iao butyl quinoline | 1 | 1 |
| Methyl ionone gamma | 15 | 15 |
| Peomosa ™ | 25 | 25 |
| Rosetone | 60 | 60 |
| Styralyl acetate | 1 | 1 |
| Terpineol alpha | 3 | 3 |
| Gamma undecalactone | 6 | 6 |
| Veramoss | 1 | 1 |
| Verdox | 40 | 40 |
| Yara Yara | 1 | 1 |
| Structure 29 | 30 | — |
| DPG | — | 30 |
| Total | 868 | 868 |

EXAMPLE XLII

The fragrance formula exemplified as follows demonstrated that 6,6,10,10-Tetramethyl-5,7,8,9,10,10a-hexahydro-6H-6a, 9-methanobenzo[H]quinazoline (Structure 29) imparted diffusive floral, soft powdery, and sweet characters.

| Ingredient | Parts (g) |
|---|---|
| Santaliff ™ | 24 |
| Phenoxanol ™ | 32 |
| Coumarin | 28 |
| Cyclamal Extra | 1 |
| Eth Vanillin | 7 |
| Geraniol 980 Pure | 1 s |
| Hedione ™ | 60 |
| Amy Cinnamic Aldehyde | 60 |
| Heliotropine | 17 |
| Hexyl Cinnamic Ald | 16 |
| Beta Ionone Extra | 6 |
| Iso E Super ™ | 70 |
| Lyral ™ | 16 |
| lillial ™ | 160 |
| Lilianth | 20 |
| Methyl Ionone Gamma A | 73 |
| Veramoss | 2 |
| Peru Balsam Oil India | 3 |
| Prenyl Acetate | 1 |
| Methyl Cedryl Ketone | 40 |
| Methyl Phenyl Acetate | 1 |
| Aubepine | 4 |
| Benzoin | 10 |
| Cedrol Tex | 3 |
| Citronellol Extra | 3 |
| Geraniol Coeur | 4 |
| Methyl Cinnamate | 3 |
| Styrax Alva Ess | 2 |
| Vanillin ex Lignin | 12 |
| *Cananga* Java Native | 5 |
| Structure 29 | 20 |
| Total | 704 |

What is claimed is:

1. A compound selected from the group consisting of: 1,1,3,3-tetramethyl-2,3,4,5-tetrahydro-1H-7,9-diaza-cyclopenta[a]naphthalene, and 1,1,3,3-tetramethyl-2,3,3a,4,5,9b-hexahydro-1H-7,9-diaza-cyclopenta[a]naphthalene.

2. A fragrance formulation containing an olfactory acceptable amount of the compound of claim 1.

3. The fragrance formulation of claim 2, wherein the fragrance formulation is incorporated into a product selected from the group consisting of a perfume, a cologne, toilet water, a cosmetic product, a personal care product, a fabric care product, a cleaning product, and an air freshener.

4. The fragrance formulation of claim 3, wherein the cleaning product is selected from the group consisting of a detergent, a dishwashing composition, a scrubbing compound, and a window cleaner.

5. The fragrance formulation of claim 2, wherein the olfactory acceptable amount is from 0.005 to 50 weight percent of the fragrance formulation.

6. The fragrance formulation of claim 2, wherein the olfactory acceptable amount is from 0.5 to 25 weight percent of the fragrance formulation.

7. The fragrance formulation of claim 2, wherein the olfactory acceptable amount is from 1 to 10 weight percent of the fragrance formulation.

8. A method of improving, enhancing, or modifying a fragrance formulation through the addition of an olfactory acceptable amount of the compound of claim 1.

9. The method of claim 8, wherein the olfactory acceptable amount is from 0.005 to 50 weight percent of the fragrance formulation.

10. The method of claim 8, wherein the olfactory acceptable amount is from 0.5 to 25 weight percent of the fragrance formulation.

11. The method of claim 8, wherein the olfactory acceptable amount is from 1 to 10 weight percent of the fragrance formulation.

* * * * *